United States Patent [19]

Bunzow et al.

[11] Patent Number: 5,547,845
[45] Date of Patent: Aug. 20, 1996

[54] AQUEOUS SOLUTION CONTAINING $D_1$ DOPAMINE RECEPTOR

[75] Inventors: James R. Bunzow; Olivier Civelli; David K. Grandy; Qun Y. Zhou, all of Portland, Oreg.

[73] Assignees: Duke University, Durham, N.C.; Oregon Health Sciences Univ., Oreg.

[21] Appl. No.: 196,523

[22] Filed: Feb. 15, 1994

Related U.S. Application Data

[62] Division of Ser. No. 908,654, Jul. 2, 1992, Pat. No. 5,389,543, which is a continuation of Ser. No. 583,852, Sep. 17, 1990, abandoned, which is a continuation-in-part of Ser. No. 523,237, May 14, 1990, abandoned.

[51] Int. Cl.$^6$ ................................................. C07K 14/705
[52] U.S. Cl. ................... 435/7.1; 435/6; 435/7.2; 530/350
[58] Field of Search ................... 435/6, 7.1, 7.2; 530/750; 436/501

[56] References Cited

U.S. PATENT DOCUMENTS 4,675,285  6/1987  Clark et al. ................... 435/6

FOREIGN PATENT DOCUMENTS

WO90/05780  5/1990  WIPO.
WO91/06557  5/1991  WIPO.

OTHER PUBLICATIONS

Nature 347:76–79, 06 Sep. 1990, Zhou et al., Cloning and Expression of Human and Rat $D_1$, Dopamine Receptors.
S. Kuffler & J. Nichols, Physiology of Neuroglial Cells, "From Neuron to Brain" Chapter Thirteen pp. 255–268 (1976).
L. L. Iversen, The Chemistry of the Brain, *Scientific American*, pp. 134–149 (Sep. 1979).
J. W. Kebabian & D. B. Calne, Multiple receptors for dopamine, *Nature* 277, pp. 93–96 (1979).
G. Shepard, Basal Ganglia, *The Synaptic Organization of the Brain* (2d Ed. 1979) pp. 268–288.
C. F. Stevens, The Neuron, *Scienctific American*, pp. 55–65 (Sep. 1979).
N. Amlaiky & M. G. Caron, Photoaffinity Labeling of the $D_2$– dopamine Receptor Using a Novel High Affinity Radioiodinated Probe, *The Journal of Biological Chemistry* 260, pp. 1983–1986 (1985).
K. Jacobs, et al., Isolation and characterization of genomic and cDNA clones of human erythropoietin, *Nature* 313, pp. 806–810 (1985).
N. Amlaiky, et al., Identification of the Binding Subunit of the $D_1$–Dopamine Receptor by Photoaffinity Crosslinking, *Molecular Pharmacology* 31, pp. 129–134 (1986).
Y. C. Yang, et al., Human IL–3 (Multi–CSF): Identification by Expression Cloning of a Novel Hematopoietic Growth Factor Related to Murine IL–3, *Cell Press* 47, pp. 3–10 (1986).

(List continued on next page.)

Primary Examiner—Garnette D. Draper
Assistant Examiner—John D. Ulm
Attorney, Agent, or Firm—Bell, Seltzer, Park & Gibson

[57] ABSTRACT

Cloned genes which code for the $D_1$ dopamine receptor are disclosed. The receptors coded for by these clones bind dopamine ligands with the proper pharmacological profile and, when expressed in the cell membrane of a suitable host and so bound, stimulate adenylyl cyclase. Also disclosed are vectors comprising a cloned gene encoding a $D_1$-dopamine receptor, cells transformed with such vectors, and oligonucleotide probes capable of selectively hybridizing to DNA comprising a portion of a gene coding for a $D_1$-dopamine receptor. The cloned genes are useful for making proteins and cell membrane preparations which can be used to screen compounds for $D_1$-dopamine receptor binding activity, are useful in molecular biology, and are useful as diagnostic probes.

8 Claims, 14 Drawing Sheets

OTHER PUBLICATIONS

B. K. Kobilka, et al., An intronless gene encoding a potential member of the family of receptors coupled to guanine nucleotide regulatory protein, *Nature* 329, pp. 75–77 (1987).

J. Watson, et al., *Molecular Biology of the Gene* (4th Ed. 1987).

Y. Masu et al., cDNA cloning of bovine substance–K receptor through oocyte expression system, *Nature* 329 pp. 836–838 (1987).

J. R. Bunzow, et al., Cloning and expression of a rat $D_2$ dopamine receptor cDNA, *Nature* 336, pp. 783–787 (1988).

A. Fargin, et al., The genomic clone G–21 which resembles a β–adrenergic receptor sequence encodes the $5-HT_{1A}$ receptor, *Nature* 335, pp. 358–360 (1988).

J. A. Gingrich, et al., Affinity Chromatography of the $D_1$ Dopamine Receptor from Rat Corpus Striatum, *Biochemistry* 27, pp. 3907–3912 (1988).

H. B. Niznik, et al., Photoaffinity Labeling of Dopamine D1 Receptors, *Biochemistry* 27, pp. 7594–7599 (1988).

J. E. Sims, et al., cDNA Expression Cloning of the IL–1 Receptor, a Member of the Immunoglobulin Superfamily, *Science* 241, pp. 585–589 (1988).

S. Stengelin, et al., Isolation of cDNAs for two distinct human Fc receptors by ligand affinity cloning, *EMBO* 7, pp. 1053–1059 (1988).

K. Yamasaki, et al., Cloning and Expression of the Human Interleukin–6 (BSF–2/IFNβ 2) Receptor, *Science* 241, pp. 825–828 (1988).

D. P. Gearing, et al., Expression cloning of a receptor for human granulocyte–macrophage colony–stimulating factor, *EMBO* 8, pp. 3667–3676 (1989).

H. Okayama, et al., [1] High–Efficiency Cloning of Full––Length cDNA; Construction and Screening of cDNA Expression Libraries for Mammalian Cells, *Methods of Enzymology* 154, pp. 3–28 (1987).

-276 GAATTCAGGGGCTTTCTGCTGCCCAAGACAGTGA
ACCATCCACGGGATTGACTTGGATTGCCACTCACTCAAGCGGTCCTCTCATGGAATGTT
TGCCTGGTGGGAGGACTCCTGGAAATCTGACTGACCCCTATTCCCTGCTTAGGA

| ATG | AGG | ACT | CTG | AAC | ACC | TCT | GCC | ATG | GAC | GGG | ACT | GGG | CTG |
|-----|-----|-----|-----|-----|-----|-----|-----|-----|-----|-----|-----|-----|-----|
| MET | Arg | Thr | Leu | Asn | Thr | Ser | Ala | Met | Asp | Gly | Thr | Gly | Leu |

| ACT | GCC | TGT | TTC | CTG | TCG | CTG | CTC | ATC | CTG | TCC | ACG | CTC | CTG |
|-----|-----|-----|-----|-----|-----|-----|-----|-----|-----|-----|-----|-----|-----|
| Thr | Ala | Cys | Phe | Leu | Ser | Leu | Leu | Ile | Leu | Ser | Thr | Leu | Leu |

| TTC | CGA | CAC | CTG | CGG | TCC | AAG | GTG | ACC | AAC | TTC | TTT | GTC | ATC |
|-----|-----|-----|-----|-----|-----|-----|-----|-----|-----|-----|-----|-----|-----|
| Phe | Arg | His | Leu | Arg | Ser | Lys | Val | Thr | Asn | Phe | Phe | Val | Ile |

| CTG | GTC | ATG | CCC | TGG | AAG | GCA | GTG | GCT | GAG | ATT | GCT | GGC | TTC |
|-----|-----|-----|-----|-----|-----|-----|-----|-----|-----|-----|-----|-----|-----|
| Leu | Val | Met | Pro | Trp | Lys | Ala | Val | Ala | Glu | Ile | Ala | Gly | Phe |

| GCC | TTT | GAC | ATC | ATG | TGC | TCC | ACT | GCA | AGA | AAG | ATG | ACC | CCC | AAG | GCA |
|-----|-----|-----|-----|-----|-----|-----|-----|-----|-----|-----|-----|-----|-----|-----|-----|
| Ala | Phe | Asp | Ile | Met | Cys | Ser | Thr | Ala | Ser | Ile | Leu | Asn | Leu |



| GCC | TTT | GAC | ATC | ATG | TGC | TCC | ACT | GCA | TCC | ATC | CTC | AAC | CTC |
|-----|-----|-----|-----|-----|-----|-----|-----|-----|-----|-----|-----|-----|-----|
| Ala | Phe | Asp | Ile | Met | Cys | Ser | Thr | Ala | Ser | Ile | Leu | Asn | Leu |

| TCC | AGC | CCT | TTC | CGG | TAT | GAG | AGA | AAG | ATG | ACC | CCC | AAG | GCA |
|-----|-----|-----|-----|-----|-----|-----|-----|-----|-----|-----|-----|-----|-----|
| Ser | Ser | Pro | Phe | Arg | Tyr | Glu | Arg | Lys | Met | Thr | Pro | Lys | Ala |

| TCT | GTA | CTC | ATC | TCC | TTC | ATC | CCA | GTG | CAG | CTC | AGC | TGG | CAC |
|-----|-----|-----|-----|-----|-----|-----|-----|-----|-----|-----|-----|-----|-----|
| Ser | Val | Leu | Ile | Ser | Phe | Ile | Pro | Val | Gln | Leu | Ser | Trp | His |

```
CCTGCAGCAAGGGAGTCAGAAGAGACAGATGTAGAAATCAAGAGTG          -199
GGTGAGGCCCCTCTGCCAGGGAAGCAATCTGGCTGTGCAAGTGC            -100
ACTTGAGGGGTGTCAGAGAGCCCCTGATGTGCTTTCTCTTAGGAAG          -1

GTG GTG GAG AGG GAC TTC TCT GTT CGT ATC CTC             75
Val Val Glu Arg Asp Phe Ser Val Arg Ile Leu             25

GGG AAC ACG CTG GTC TGT GCT GCC GTT ATC AGG             150
Gly Asn Thr Leu Val Cys Ala Ala Val Ile Arg             50

TCC TTG GCT GTG TCA GAT CTC TTG GTG GCC GTC             225
Ser Leu Ala Val Ser Asp Leu Leu Val Ala Val             75

TGG CCC TTT GGG TCC TTC TGT AAC ATC TGG GTG             300
Trp Pro Phe Gly Ser Phe Cys Asn Ile Trp Val             100

TGT GTG ATC AGC GTG GAC AGG TAT TGG GCT ATC             375
Cys Val Ile Ser Val Asp Arg Tyr Trp Ala Ile             125

GCC TTC ATC CTG ATC AGT GTG GCA TGG ACC TTG             450
Ala Phe Ile Leu Ile Ser Val Ala Trp Thr Leu             150

AAG GCA AAA CCC ACA AGC CCC TCT GAT GGA AAT             525
Lys Ala Lys Pro Thr Ser Pro Ser Asp Gly Asn             175
```

```
GCC ACT TCC CTG GCT GAG ACC ATA GAC AAC TGT GAC TCC AGC
Ala Thr Ser Leu Ala Glu Thr Ile Asp Asn Cys Asp Ser Ser

ATA AGC TTT TAC ATC CCT GTG GCC ATC ATG ATT GTC ACC TAC
Ile Ser Phe Tyr Ile Pro Val Ala Ile Met Ile Val Thr Tyr

CGG CGC ATT GCG GCC TTG GAG AGG GCA GCA GTC CAC GCC AAG
Arg Arg Ile Ala Ala Leu Glu Arg Ala Ala Val His Ala Lys

GTC GAA TGT TCT CAA CCG GAA AGT TCT TTT AAG ATG TCC TTC
Val Glu Cys Ser Gln Pro Glu Ser Ser Phe Lys Met Ser Phe

GTG ATC ATG GGT GTG TTT GTG TGC TGT TGG CTA CCT TTC TTC
Val Ile Met Gly Val Phe Val Cys Cys Trp Leu Pro Phe Phe

GGG GAG ACG CAG CCC TTC TGC ATT GAT TCC AAC ACC TTT GAC
Gly Glu Thr Gln Pro Phe Cys Ile Asp Ser Asn Thr Phe Asp

TTG AAC CCC ATC ATT TAT GCC TTT AAT GCT GAT TTT CGG AAG
Leu Asn Pro Ile Ile Tyr Ala Phe Asn Ala Asp Phe Arg Lys

TGC CCT GCG ACG AAT AAT GCC ATA GAG ACG GTG AGT ATC AAT
Cys Pro Ala Thr Asn Asn Ala Ile Glu Thr Val Ser Ile Asn
```

TO FIG. 1B(II) CONTINUED

```
CTC AGC AGG ACA TAT GCC ATC TCA TCC TCT GTA         600
Leu Ser Arg Thr Tyr Ala Ile Ser Ser Ser Val        200

ACC AGG ATC TAC AGG ATT GCT CAG AAA CAA ATA         675
Thr Arg Ile Tyr Arg Ile Ala Gln Lys Gln Ile        225

AAT TGC CAG ACC ACA GGT AAT GGA AAG CCT             750
Asn Cys Gln Thr Thr Gly Asn Gly Lys Pro            250

AAA AGA GAA ACT AAA GTC CTG AAG ACT CTG TCG         825
Lys Arg Glu Thr Lys Val Leu Lys Thr Leu Ser        275

ATC TTG AAC TGC ATT TTG CCC TTC TGT GGG TCT         900
Ile Leu Asn Cys Ile Leu Pro Phe Cys Gly Ser        300

GTG TTT GTG TGG TTT GGG TGG GCT AAT TCA TCC         975
Val Phe Val Trp Phe Gly Trp Ala Asn Ser Ser        325

GCA TTT TCA ACC CTC TTA GGA TGC TAC AGA CTT        1050
Ala Phe Ser Thr Leu Leu Gly Cys Tyr Arg Leu        350

AAC AAT GGG GCC GCC ATG TTT TCC AGC CAT CAT        1125
Asn Asn Gly Ala Ala Met Phe Ser Ser His His        375
```

FROM FIG. 1B(II).

FIG. 1B(II) CONTINUED.

```
GAG CCA CGA GGC TCC ATC TCC AAG GAG TGC AAT CTG GTT TAC
Glu Pro Arg Gly Ser Ile Ser Lys Glu Cys Asn Leu Val Tyr

CTG AAA AAG GAG GAG GCA GCT GGC ATC GCC AGA CCC TTG GAG
Leu Lys Lys Glu Glu Ala Ala Gly Ile Ala Arg Pro Leu Glu

TAT GAC ACT GAC GTC TCT CTG GAG AAG ATC CAA CCC ATC ACA
Tyr Asp Thr Asp Val Ser Leu Glu Lys Ile Gln Pro Ile Thr

AATCCTGCCACACATGCTCATCCCAAAAGCTAGAGGAGATTGCTCTGGGCTTGCT
GCCCTCTGCTGTCCAACACACAATTAACTCCGTTCCAAATACATTCCAGTGT
ACATGGGAGCCATAAGGGACATGTCTTTGGCTTCAGAATTGTTTTAGAAATTA
GAACAGCTTCACTTAAAATCAAATTTTCTGGGAAGAAATGAGATGGGTTGAGTT
TCAGATTGTAAGGTAGGTGCATGCCTTCATAAATTATTCTAAAACATTAATTGA
TGTTTTGTTGATATTGGTTCTATTTATTGTATATGGATATTTTAATTTA
AATGAGTTTTATCCAAGACCTTACAACACCACATTTCTGGCCATTAACTAGCACTTT
TGTTCAGTGTAACTTCTAGAAAACTGATAAATGCTATAAATGCTTTCTTTTCTGAAAGATTTGAAAAATT
CAAATGACTTTCCCAGGGAATTTGCAGTTCTGTAAATAATAATTGGCCCTCTCCATCTTT
TGAAAAGTATATGCTGCTTTGTATTTATGCACAGACAGTGGGTTACAGCAGCCACTGAGG
CTTCCTGGAGAGAGATCTGTAGCACAGACAGTGCTTAATCTGAATTTAGAGCTGATT
AAACCAGTCAGTGGGGCTACTTTCTGAGTCAGATACTTCTGTTGATGGGAGAAACAGAAG
TAGTGCCTCATTATCATTCTTGACAAATGCTAGTCCTTTCTCTGCTTGGAATCAGGTTCCTGCA
CATCTCTTTTGACAAATCGTGGGGCATTCAACAGAGTTTCTTTGAAATGTTTACAACGTATT
GATGCCAACTCGTGGGCATTCAACAGAGTTTCTTTGAAATGTTTACAACGTATT
AAAGAGAAAAAAATCTGAAAAATATCTCCTGCATCAGGTCTGTGTTATTGTA
ACATAATAAAATATTTTGTGACGGAATTC  3065
```

TO FIG. 1B(III) CONTINUED

FIG. 1B(III).

```
CTG ATC CCA CAT GCT GTG GGC TCC TCT GAG GAC          1200
Leu Ile Pro His Ala Val Gly Ser Ser Glu Asp           400

AAG CTG TCC CCA GCC CTA TCG GTC ATA TTG GAC          1275
Lys Leu Ser Pro Ala Leu Ser Val Ile Leu Asp           425

CAA AAC GGT CAG CAC CCA ACC TGA ACTCGGCAGATG         1352
Gln Asn Gly Gln His Pro Thr  ;                        446

ATTAAGAAACTAAGGTACGGTGAGACTCTGAGGTGTCAGGAGA          1451
ATTTCTGTGTGTTCATAGTCAATCAAACAGGACACTACAA             1550
TTCTTATCTTAGGATTTACCAAGTCAAATAGGCAAAGAATCAACAGT      1649
TGCTGTATACAAACAGGTGCTAACACTGTTCCCAGCAAGTTT           1748
GGCTTACAGTAGGAGTGAGAAATTTTCCAGAATTGAGAGA             1847
TGATATAATAAATGAAGCAAACACAGACTCTGTGAGATAAATT          1946
ATAAGCCAATGATTCCTTAAAATTCATGGACACAGATAAATGCAAGG      2045
TGAAATGATTCCTTAAAATTCATGGACACAGATAAATGCAAGG          2144
TAAAAAAGTATAGCTACTGTGTTCAAAACGTTTAAATGA              2243
CTTAAGAGAGCCCAGCATTAAATTACGATCTTAGGTGGTAA            2342
CTCATTTCATGTGTCAGGTAGTTTTTCTGAACCACACAAATGG          2441
GACCAAACTCAAACCCTGCATTTCCATCTTACCAGTCAAACC           2540
TTTAAAGGAGTCTTTAAATGTTAATGGTATACTAACTAACGAA          2639
AATCCTTCCCTTGGGTGTGTTGAGCTCCCCAAAGCCATCAG            2738
TCATCACCCGGACTGTAAAAAGTATCATAAGCCTCCCTTGCCA          2837
CTTCTTGATAAGCAATGAACTTAGATCATTAGATGCAATCCGTG         2936
TTGTGAATGTTTCTTAATTTTATTTTATTGGCTGTATGCTTTCTTAC      3035
```

FIG. 1B(III) CONTINUED.

FROM FIG. 1B(III).

FIG. 3A.

FROM FIG. 3A.

FIG. 3A (CONTINUED 1).

FROM FIG. 3A (CONTINUED 1).

```
                                                                                              359
IleTyrAlaPheAsnAlaAspPheArgLysAlaPheSerThrLeuLeuGlyCysTyrArgLeuCysProAlaThrAsnAsnAlaIleGlu
ATTTATGCCTTTAATGCTGATTTTCGGAAGGCATTTTCAACCCTCTTAGGATGCTACAGACTTTGCCCTGCGACGAATAATGCCATAGAG
   T             C  C  A    G  C                   C                 A T             1077
                     Gln                                              Thr
                                                                                              389
ThrValSerIleAsnAsnAsnGlyAlaAlaMETPheSerSerHisHisGluProArgGlySerIleSerLysGluCysAsnLeuValTyr
ACGGTGAGTATCAATAACAATGGGGCCGCCATGTTTTCCAGCCATCATGAGCCACGAGGCTCCATCTCCAAGGAGTGCAATCTGGTTTAC
         C  T  C                        T  G                 C                       C  T  1167
                                         ValVal                                       Asp
                                                                                              419
LeuIleProHisAlaValGlySerSerGluLeuLysLysGluGluAlaAlaGlyIleAlaArgProLeuGluLysLeuSerProAla
CTGATCCCACATGCTGTGGGCTCCTCTGAGGACCTGAAAAAGGAGGAGGCAGCAGCTGGCATCGCCAGACCCTTGGAGAAGCTGTCCCCAGCC
       T  C                                 G           A      T  AG  C                   1257
                                                                Gly           Lys
                                                            446
LeuSerValIleLeuAspTyrAspThrAspValSerLeuGluLysIleGlnProIleThrGlnAsnGlyGlnHisProThr
CTATCGGTCATATTGGACTATGACACTGACGTCTCTCTGGAGAAGATCCAACCCATCACACAAAACGGTCAGCACCCAACCTGAACTCGCAG
T                              C  T    A       A        TG  C GT A        T  T  C  T       1349
                                                            Val  HisSer              Ser
ATGAATCTGCCACACATGCTCATCCCAAAAGCTAGAGGAGATTGCTCTGGGGTTTGCTATTAAGAAACTAAGGTACGGTGAGACTCGAGGTGTCAGGAGACTCGAGAGCCCTCTGCTTTCC
                                                                                                              1468
AACACACAATTAACTCCGTTTCCAAATACATTCCAGTGTATTTCTGTGTTCATAGTCAATCAAACAGTGAACAGCTTCACTTAAAATCAAATTTCTGGAAGAAAATGAGATGGGTTGAGTTT
                                                                                                              1587
AATTGTTTTAGAAATTTATTCTTATCTTAGGATTTACCAAATAGGCAAAGATCAACAGTGAACAGCTTCATGCCTTCATAAATTATTTCTAAAACATTAATTGAGGCTTACAGTAGGAGTGAGAA
                                                                                                              1706
GCTGTATACAAACAGGTGCTAACACTGTTCCCAGCAAAGTTTTCAGATTGGTTCTATTATTTATTTGTATATATGGATATATTTAATTAATAAATAAATATATATTAATCATATTTAATAGGATAAA
                                                                                                              1825
ATTTTTTCCAGAATTGAGAGATGTTTTGTTGATATTTTGTTGATATTGGTTCTATTATTTATTTGTATATATGGATATATTTAATTAATAAATAAATATATATTAATCATATTTAATAGGATAAA
AGA                                                                                                           1944
TTAAATGAGTTTTATCCAAGACCTTACAACCACATTTCTGGCCATTTAACTAGCACTTATAAGCCAATGAAGCAAACACAGACTCTGTGAGATTCTAAATGTTCATGTGTAACTTCT
                                                                                                              2063
```

AQUEOUS SOLUTION CONTAINING D₁ DOPAMINE RECEPTOR

This work was supported in part by National Institutes of Health Grants Numbers NS19576, MH45614, and DK34231. The government may have certain rights to this invention.

This application is a divisional of continuation application Ser. No. 07/908,654, filed Jul. 2, 1992, now U.S. Pat. No. 5,389,543, the disclosure of which is incorporated by reference herein in its entirety, which is a continuation of application Ser. No. 07/583,852, filed Sep. 17, 1990 (abandoned), which is a continuation-in-part of application Ser. No. 07/523,237, filed May 14, 1990 (abandoned).

BACKGROUND OF THE INVENTION

Dopamine is a neurotransmitter which participates in a variety of different functions mediated by the nervous system, including vision, movement, and behavior. See generally Cooper, J. et al., The Biochemical Basis of Neuropharmacology, 161–195 (Oxford University Press, NY 3d Ed. 1978). The diverse physiological actions of dopemine are in turn mediated by its interaction with two basic types of G protein-coupled receptors: $D_1$ and $D_2$, which respectively stimulate and inhibit the enzyme adenylyl cyclase. Kebabian, J. and Calne, D., Nature 277, 93–96 (1979). Alterations in the number or activity of these receptors may be a contributory factor in disease states such as Parkinson's disease (a movement disorder) and schizophrenia (a behavioral disorder).

A great deal of information has accumulated on the biochemistry of the $D_1$- and $D_2$- dopamine receptors, and methods have been developed to solubilize and purify these receptor proteins. See Senogles, S. et al., Affinity Chromatography of the Anterior Pituitary $D_2$ Dopamine Receptor, Biochemistry 25, 749–753 (1986); Senogles, S. et al., Purification and Characterization of the $D_2$ Dopamine Receptor from Bovine Anterior Pituitary, J. Biol. Chem. 263, 18996–19002 (1988); Gingrich, J. et al., Affinity Chromatography of the $D_1$ Dopamine Receptor from Rat Corpus Striatum, Biochemistry 27, 3907–3912 (1988); Gingrich, J. et al., Complete Purification of the $D_1$ Dopamine Receptor from Rat Striatum (in press). The $D_1$ dopamine receptor in several tissues appears to be a glycosylated membrane protein of about 72 kDa. Amlaiky, N. et al., Mol. Pharmacol. 31, 129–134 (1987); Ninik, H. et al., Biochemistry 27, 7594–7599 (1988). The $D_2$ receptor has been suggested to have a higher molecular weight of about $M_r$ 90–150 kDa. Amlaiky, N. and Caron, M., J. Biol. Chem. 260, 1983–1986 (1985); Amlaiky, N. and Caron, M., J. Neurochem. 47, 196–204 (1986); Jarvie, K. et al., Mol. Pharmacol. 34, 91–97 (1988).

The cloning of the cDNA for a rat $D_2$ dopamine receptor has recently been reported. See Bunzow, J. et al., Nature 336, 783–787 (1988); see also Civelli, O. et al., PCT Appln. WO 90/05780. This clone was obtained while probing for opiate receptors using the techniques of low stringency hybridization with the $\beta_2$-Adrenergic receptor cDNA. Ligand binding studies of this receptor, expressed in a mouse cell line, indicate that it binds ligands with appropriate $D_2$ specificity. No clone for the $D_1$-dopamine receptor has yet been reported in the literature.

SUMMARY OF THE INVENTION

The present invention is based on our ongoing research into the dopamine receptor family. Disclosed herein are cloned genes which code for the $D_1$ dopamine receptor (i.e., isolated and purified DNA sequences which code for the $D_1$ dopamine receptor). The receptors coded for by these clones bind dopamine ligands with the proper pharmacological profile and, when expressed in the cell membrane of a suitable host and so bound, stimulate adenylyl cyclase.

A second aspect of the present invention is a vector comprising a cloned gene encoding a $D_1$-dopamine receptor.

A third aspect of the present invention is a cell transformed with a vector, the vector comprising a cloned gene encoding a $D_1$-dopamine receptor.

A fourth aspect of the present invention is an aqueous solution containing cell membranes, the cell membranes containing a $D_1$-dopamine receptor and adenylyl cyclase, wherein the cell membranes are free of $D_2$-dopamine receptors, and wherein the $D_1$-dopamine receptors are capable of stimulating the adenylyl cyclase on binding a $D_1$-dopamine receptor agonist.

A fifth aspect of the present invention is an assay procedure comprising the steps of: (a) providing an aqueous solution containing cell membranes as described above; then (b) adding a test compound to the aqueous solution; and then (c) monitoring the activity of adenylyl cyclase in the aqueous solution.

A sixth aspect of the present invention is an oligonucleotide probe capable of selectively hybridizing to DNA, which DNA comprises a portion of a gene coding for a $D_1$-dopamine receptor, which probe is labelled with a detectable group.

The foregoing and other aspects of the present invention are explained in greater detail in the drawings, detailed description, and examples set forth below.

BRIEF DESCRIPTION OF THE DRAWINGS

FIGS. 1A and 1B (I) to 1B (III) shows the restriction map (1A) and nucleotide and deduced amino acid sequence (1B) of a human $D_1$ dopamine receptor clone. The sequence shown in FIG. 1B (I) to 1B (III) was obtained from D233, a cDNA clone from a human retina library, and HGL26, a human genomic clone. These two clones overlap as indicated in (1A). No differences were detected in the overlapping sequences of these clones. Restriction endonuclease sites are indicated. The 3' EcoRI site is an insertion site of the retinal cDNA clone into the k arms. The stippled bars denote the coding region. Nucleotide sequence (1B) is numbered in the 5' to 3' direction beginning with the first ATG of the open reading frame. Preceding bases are indicated by negative numbers. Nucleotides are numbered at the right-hand end of each line. The deduced amino acid sequence, shown below the nucleotide sequence, is numbered at the right-hand end of each line beginning with the initiator methionine (Met). Hydrophobic segments representing putative membrane domains are underlined. Putative sites of N-linked glycosylation are indicated by double underlines. In the 3' untranslated region, several polyadenylation signals are found (beginning at bp 1910, 2288, 2341, 2907, and 3040).

FIG. 3A shows the nucleotide and deduced amino-acid sequences of the human and rat $D_1$ dopamine receptors as determined from clone HGR213-1. Numbering begins with the first methionine of the open reading frame and is beneath the nucleotide sequence. The deduced amino-acid sequence of human $D_1$ receptor is shown above the nucleotide sequence. For rat $D_1$ sequences, the coding region and their differences with human $D_1$ are shown below the human $D_1$ sequences. The postulated N-glycosylation sites are indicated by asterisks and the putative protein kinase A phosphorylation sites have a line above them. Dotted lines denote deletion.

FIG. 3B shows the alignment of the amino-acid sequence of the human $D_1$, human $D_2$, human $β_2$, human $β_1$, hamster $α_1$, human $α_{2A}$ and human $α_{2B}$ receptors. Shaded amino acids represent residues that are conserved in at least three receptors and the $D_1$. The putative transmembrane domains are bracketed and labelled by Roman numerals. The number of residues in the variable third cytoplasmic loop and at the C-terminus are shown in parentheses.

DETAILED DESCRIPTION OF THE PREFERRED EMBODIMENTS

Figure 3A:
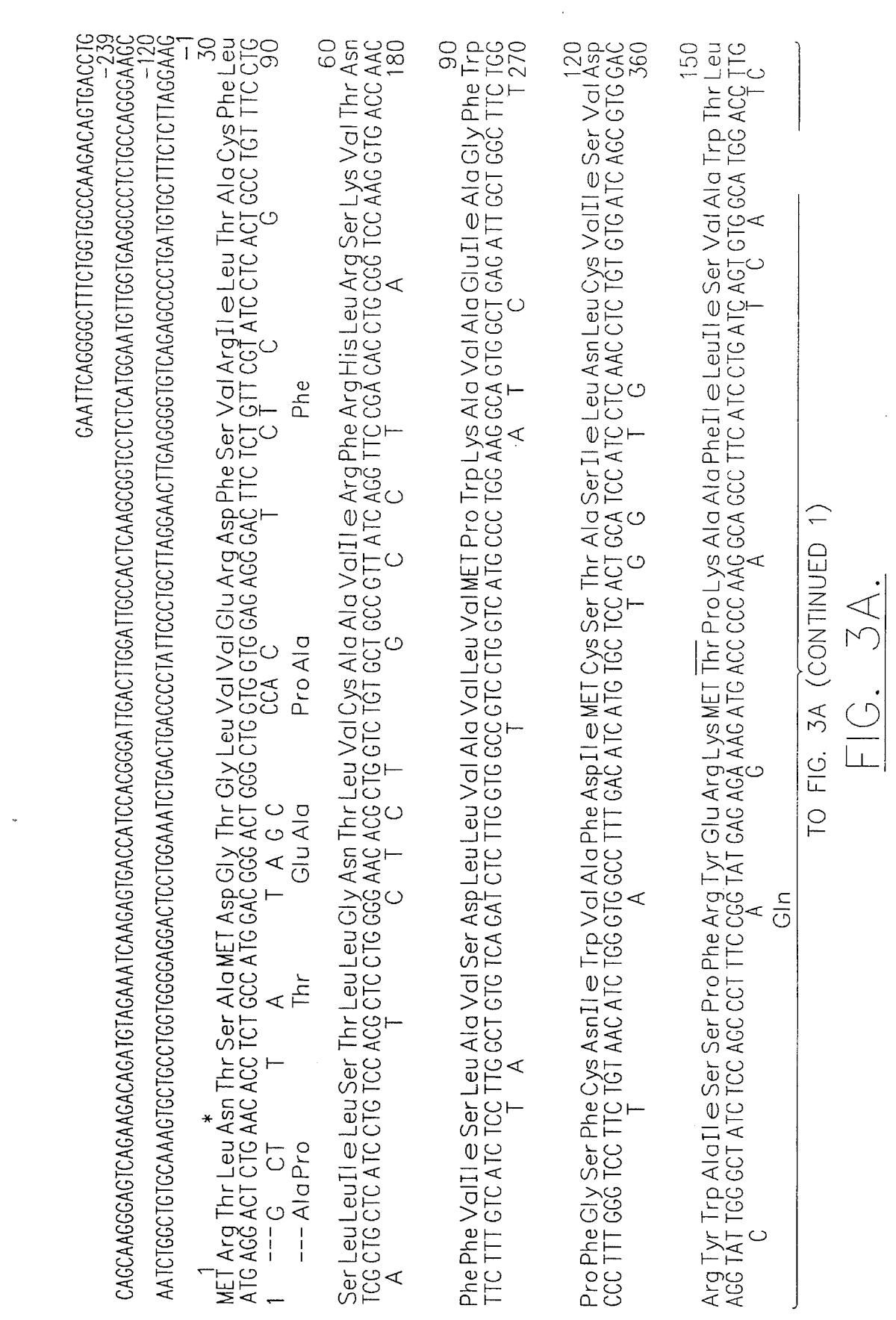
Figure 1A:
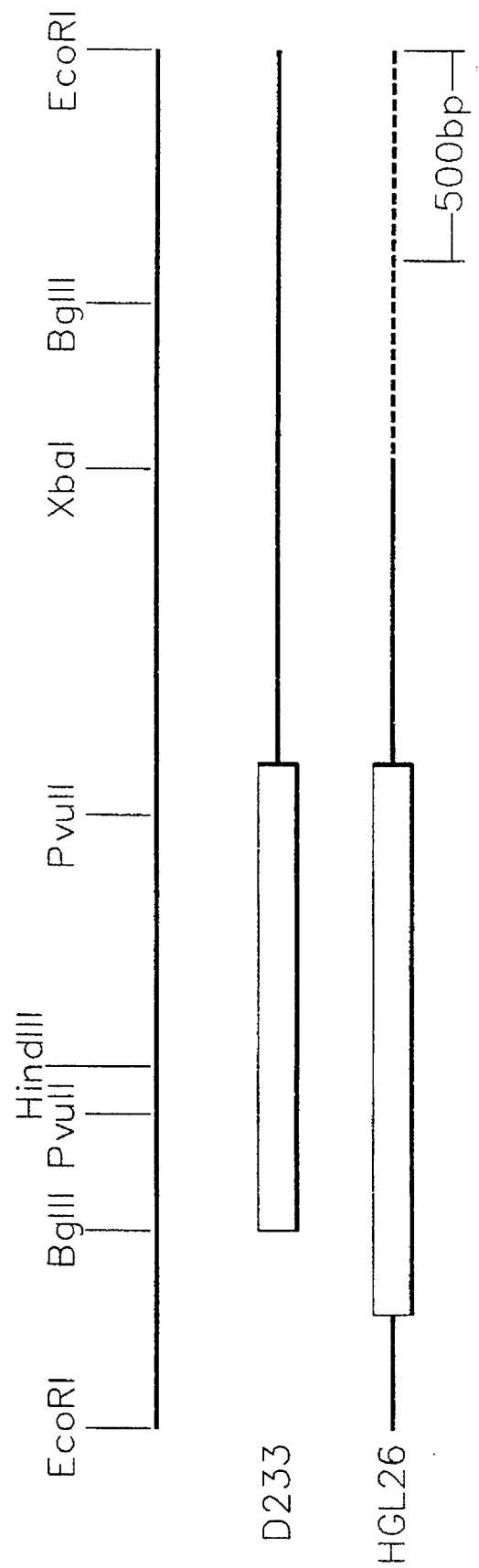

The term "$D_1$-dopamine receptor" as used herein refers to proteins substantially homologous to, and having substantially the same biological activity as, the protein coded for by the nucleotide sequence depicted in either FIG. 1B or 3A (i.e., proteins which stimulate adenylyl cyclase on binding dopamine). This definition is intended to encompass natural allelic variations in the $D_1$-dopamine receptor sequence. Cloned genes of the present invention may code for $D_1$-dopamine receptors of any species of origin, including mouse, rat, rabbit, cat, and human, but preferably code for receptors of mammalian origin.

Nucleotide bases are abbreviated herein as follows:

| A = Adenine | G = Guanine |
|---|---|
| C = Cytosine | T = Thymine |

Amino acid residues are abbreviated herein to either three letters or a single letter as follows:

| Ala; A = Alanine | Leu; L = Leucine |
|---|---|
| Arg; R = Arginine | Lys; K = Lysine |
| Asn; N = Asparagine | Met; M = Methionine |
| Asp; D = Aspartic acid | Phe; F = Phenylalanine |
| Cys; C = Cysteine | Pro; P = Proline |
| Gln; Q = Glutamine | Ser; S = Serine |
| Glu; E = Glutamic acid | Thr; T = Threonine |
| Gly; G = Glycine | Trp; W = Tryptophan |
| His; H = Histidine | Tyr; Y = Tyrosine |
| Ile; I = Isoleucine | Val; V = Valine |

The production of proteins such as the $D_1$-dopamine receptor from cloned genes by genetic engineering is well known. See, e.g. U.S. Pat. No. 4,761,371 to Bell et al. at Col. 6 line 3 to Col. 9 line 65. (The disclosure of all patent references cited herein is to be incorporated herein by reference.) The discussion which follows is accordingly intended as an overview of this field, and is not intended to reflect the full state of the art.

DNA which encodes the $D_1$-dopamine receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the $D_1$-dopamine receptor gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, $D_1$-dopamine receptor gene sequences may be recovered by use of the polymerase chain reaction (PCR) procedure, with the PCR oligonucleotide primers being produced from the $D_1$-dopamine receptor gene sequence provided herein. See U.S. Pat. Nos. 4,683,195 to Mullis et al. and U.S. Pat. No. 4,683,202 to Mullis.

The $D_1$-dopamine receptor may be synthesized in host cells transformed with vectors containing DNA encoding the $D_1$-dopamine receptor. A vector is a replicable DNA construct. Vectors are used herein either to amplify DNA encoding the $D_1$-dopamine receptor and/or to express DNA which encodes the $D_1$-dopamine receptor. An expression vector is a replicate DNA construct in-which a DNA sequence encoding the $D_1$ receptor is operably linked to suitable control sequences capable of effecting the expression of the $D_1$ receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the $D_1$ receptor vectors constructed using recombinant DNA techniques. Transformed host cells ordinarily express the $D_1$ receptor, but host cells transformed for purposes of cloning or amplifying the $D_1$ receptor DNA need not express the $D_1$ receptor. When expressed, the $D_1$ receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in reading phase.

Suitable host cells include prokaryotes, yeast cells or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), and *E. coli* 294 (ATCC 31,446). Pseudomonas species, Bacillus species, and *Serratia marcesans* are also suitable.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., Gene 2, 95 (1977). pBR322 contains genes for ampicillin and tetracycline resistance and thus provides easy means for identifying transformed cells. Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., Nature 275, 615 (1978); and Goeddel et al., Nature 281, 544 (1979)), a tryptophan (trp) promoter system (Goeddel et al., Nucleic Acids Res. 8, 4057 (1980) and EPO App. Publ. No. 36,776) and the tac promoter (H. De Boer et al., Proc. Natl. Acad. Sci. USA 80, 21 (1983)). While these are commonly used, other microbial promoters are suitable. Details concerning nucleotide sequences of many have been published, enabling a skilled worker to operably ligate them to DNA encoding the $D_1$ receptor in plasmid or viral vectors (Siebenlist et al., Cell 20, 269 (1980)). The promoter and Shine-Dalgarno sequence (for prokaryotic host expression) are operably linked to the DNA encoding the the $D_1$ receptor, i.e., they are positioned so as to promote transcription of the $D_1$ receptor messenger RNA from the DNA.

Eukaryotic microbes such as yeast cultures may be transformed with suitable $D_1$ receptor-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the $D_1$ receptor, sequences for polyadenylation and transcription termination, and a selection gene. An exemplary plasmid is YRp7, (Stinchcomb et al., Nature 282, 39 (1979); Kingsman et al., Gene 7, 141 (1979); Tschemper et al., Gene 10, 157 (1980)). This plasmid contains the trpl gene, which provides a selection marker for a mutant strain of yeast lacking the ability to grow in tryptophan, for example ATCC No. 44076 or PEP4-1 (Jones, Genetics 85, 12 (1977)). The presence of the trpl lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., J. Biol. Chem. 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes may also be ligated into the expression vector 3' of the the $D_1$ receptor coding sequences to provide polyadenylation and termination of the mRNA.

Cultures of cells derived from multicellular organisms are a desirable host for recombinant $D_1$-dopamine receptor synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g. U.S. Pat. No. 4,599,308. The early and late promoters are useful because both are obtained easily from the virus as a fragment which also contains the SV40 vital origin of replication. See Fiers et al., Nature 273, 113 (1978). Further, the human genomic $D_1$ receptor promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Rather than using vectors which contain viral origins of replication, one can transform mammalian cells by the method of cotransformation with a selectable marker and the $D_1$ receptor DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

$D_1$-dopamine receptors made from cloned genes in accordance with the present invention may be used for screening compounds for $D_1$ dopamine receptor activity, or for determining the amount of a dopaminergic drug in a solution (e.g., blood plasma or serum). For example, host cells may be transformed with a vector of the present invention, $D_1$-dopamine receptors expressed in that host, the cells lysed, and the membranes from those cells used to screen compounds for $D_1$-dopamine receptor binding activity. Competitive binding assays in which such procedures may be carried out are well known, as illustrated by the Examples below. By selection of host cells which do not ordinarily express a dopamine receptor, preparations free of $D_2$ receptors can be obtained. Further, $D_1$-dopamine receptor agonists and antagonists can be identified by transforming host cells with vectors of the present invention, which host cells also express adenylyl cyclase. Membranes obtained from such cells can be used in binding studies wherein the activity of the adenylyl cyclase is monitored. $D_1$ receptor agonists will stimulate the adenylyl cyclase such cells must be capable of operatively associating the $D_1$-dopamine receptor with the adenylyl cyclase, i.e., G protein must also be present in the cell membranes. Procedures for carrying out assays such as these are also described in greater detail in the Examples which follow.

Cloned genes and vectors of the present invention are useful in molecular biology to transform cells which do not ordinarily express the $D_1$-dopamine receptor to thereafter express this receptor. Such cells are useful as intermediates for making cell membrane preparations useful for receptor binding assays, which are in turn useful for drug screening. Further, genes and vectors of the present invention are useful in gene therapy. For such purposes, retroviral vectors as described in U.S. Pat. No. 4,650,764 to Temin and Watanabe or U.S. Pat. No. 4,861,719 to Miller may be employed. Cloned genes of the present invention, or fragments thereof, may also be used in gene therapy carried out by homologous recombination or site-directed mutagenesis. See generally Thomas, K. and Capecchi, M., Cell 51, 503–512 (1987); Bertling, W., Bioscience Reports 7, 107–112 (1987); Smithies, O. et al., Nature 317, 230–234 (1985).

Cloned genes of the present invention, and oligonucleotides derived therefrom, are useful for screening for restriction fragment length polymorphism (RFLP) associated with certain disorders.

Oligonucleotides of the present invention are useful as diagnostic tools for probing $D_1$-receptor gene expression in nervous tissue. For example, tissue can be probed in situ with oligonucleotide probes carrying detectable groups by conventional autoradiography techniques, as explained in greater detail in the Examples below, to investigate native expression of this receptor or pathological conditions relating thereto. Further, chromosomes can be probed to investigate the presence or absence of a $D_1$-dopamine receptor gene, and potential pathological conditions related thereto, as also illustrated by the Examples below.

The Examples which follow are illustrative of specific embodiments of the invention, and various uses thereof. They are set forth for explanatory purposes only, and are not to be taken as limiting the invention.

EXAMPLE 1

Cloning of $D_1$ Receptor Gene Clone HGL26

This example describes the isolation and characterization of a gene encoding a human $D_1$ dopamine receptor. This gene is intronless within its coding region, in contrast to that encoding the $D_2$ dopamine receptor. This $D_1$ receptor gene encodes a protein of 446 amino acid residues having a predicted molecular weight of 49,300 daltons and has a transmembrane topology similar to that of other G protein-coupled receptors.

To isolate a gene for a $D_1$ dopamine receptor, a human retina cDNA library was screened at low stringency with an oligonucleotide probe derived from the the rat striatal $D_2$ dopamine receptor. Dopamine is the predominant catecholamine in retinal tissue, and there are abundant levels of both $D_1$ and $D_2$ receptors. See Ehinger, B. Prog. Retinal Res. 2, 213–232 (1983); Gredal, O. et al., Eur. J. Pharmacol. 137, 241–245 (1987); McGonigle, P. et al., Invest. Ophthalmol.Vis. Sci. 29, 687–694 (1988).

Clone D233 was obtained by screening $2 \times 10^6$ recombinants from a human retina cDNA library in kgt10 (provided by Dr. Jeremy Nathans, Johns Hopkins University) with a synthetic 72-base oligonucleotide probe derived from nucleotides 199–270 of a rat striatal $D_2$ dopamine receptor clone. This probe corresponds to the second transmembrane domain (amino acids 67–92) of the rat striatal $D_2$ dopamine receptor. See Bunzow, J., et al., Nature 336, 783–787 (1988). The probe was purified on a denaturing polyacrylamide gel and labeled with $^{32}P$ at the 5' hydroxyl group by T4 polynucleotide kinase. Duplicate nitrocellulose filters were hybridized in 2X SSC, 10X Denhardt's, 0.1% sodium pyrophosphate, 0.1% SDS, 50 μg/ml sheared salmon sperm DNA, and $^{32}P$-labeled oligonucleotide ($2$–$10 \times 10^6$ cpm/ml) at 42° C. for 18 hr. Filters were washed at 60° C. in 1X SSC. From this library, a clone (D233) was isolated that contained a 2.9 kb insert. D233 encoded an open reading frame that was highly homologous to other G protein-coupled receptors.

D233 appeared to be a partial clone lacking sequences homologous to the first transmembrane and amino terminal regions of these receptors. The gene encoding this protein was judged to be intronless based on Southern blot analysis of human genomic DNA probed with a 0.7 kb PvuII restriction fragment of D233 at high stringency. Consequently, a human genomic DNA library was screened using this PvuII fragment. The PvuII restriction sites are shown in FIG. 1A.

The 0.7 kb PvuII restriction fragment from clone D233 was random-labeled with [$^{32}P$]dCTP and used to probe duplicate filters lifted from a human genomic library in EMBL3 (Clontech) under the following conditions: 50% formamide, 5× SSC, 5× Denhardt's, 25 mM sodium phosphate, 0.1% sodium pyrophosphate, 0.1% SDS, 50 1 g/ml sheared salmon sperm DNA, 100 1 g/ml tRNA, 10% dextran sulfate, 42° C., 18 hr. Filters were washed at 55° C. in 1× SSC. Nucleotide sequencing was performed by the Sanger dideoxy method using Sequenase (U.S. Biochemical Corp.).

A 2.3 kb EcoRI-XbaI restriction fragment from one (HGL26) of three isolated clones was subcloned and sequenced. HGL26 possessed a nucleotide sequence extending beyond the 5' end of D233 and contained a likely site of translational initiation.

FIGS. 1A and 1B show the restriction map, nucleotide sequence (3341 bp), and deduced amino acid sequence derived from the overlapping sequences of genomic clone HGL26 and retinal cDNA clone D233. The first ATG triplet downstream of nonsense codons found in frame with the rest of the coding block and having a Kozak consensus sequence was assigned as the site of translational initiation. See generally Kozak, M. Nucleic Acids Res. 12, 857–872 (1984). The open reading frame extends for 1338 bp (446 amino acids).

Features of interest within this receptor are several potential sites of post-translational modification. These include two consensus sites for N-linked glycosylation (Asn 5 and Asn 175). See generally Hubbard, S. and Ivatt, R. Ann. Rev. Biochem. 50,555–583 (1981). The presence of these glycosylation sites may account for the difference between the calculated molecular weight (49,300 daltons) of this protein and the apparent size ($M_r$=72,000) of the $D_1$ dopamine receptor from rat striatum as revealed by photoaffinity crosslinking. Amlaiky, N. et al., Mol. Pharmacol. 31, 129–134 (1987). In addition, the $D_1$ receptor contains a cysteine residue (Cys 351) in the carboxyl terminus near transmembrane VII that is conserved in most G protein-coupled receptors and may be palmitoylated, as in the $\beta_2$-adrenergic receptor and rhodopsin. See O'Dowd, B. et al., J. Biol. Chem. 264, 7564–7569 (1989); Ovchinnikov, Y. et al., FEBS Lett. 230, 1–5 (1988). Furthermore, several consensus sites for regulatory phosphorylation are found in the predicted cytoplasmic domains of this protein. See Caron, M. et al., In: G Proteins (Academic Press, Orlando, Fla., 1990, pp. 295–316). The third cytoplasmic loop (residues 265–268) and carboxyl tail (residues 338–343) each contain a putative site for phosphorylation by protein kinase A. In addition, the carboxyl tail contains several putative sites for phosphorylation by an agonist-dependent receptor kinase such as $\beta$-adrenergic receptor kinase or rhodopsin kinase. These observations are consistent with the idea that phosphorylation of the $D_1$ receptor may have a role in regulating its functional activity.

COMPARATIVE EXAMPLE A

Structural Comparison of the Protein Coded For by Clone HGL26 with Other G Protein-Coupled Receptors The $D_1$ dopamine receptor encoded by clone HGL26 possesses several features characteristic of G protein-coupled receptors. Hydropathicity analysis of the protein sequence revealed the presence of the typical seven hydrophobic segments of 20–27 amino acids that presumably represent transmembrane domains. Within these regions, the human $D_1$ dopamine receptor has a sequence identity of 40–43% with the human $D_2$ receptor, $\alpha_2$-, $\beta_1$-, and $\beta_2$-adrenergic receptors, and $5HT_{1A}$ receptor. The most homologous regions shared by the human $D_1$ and $D_2$ receptors are found in transmembrane segments II and III (57% identity). Previous site-directed mutagenesis studies suggest that an Asp residue in membrane III (Asp 113) and two serine residues in membrane V (Ser 204 and Ser 207) of $\beta$-adrenergic receptors respectively interact with the amino and catechol hydroxyl groups of catecholamines. See Dixon, R. et al., Nature 326, 73–77 (1987); Strader, C. et al., J. Biol. Chem. 264, 13572–13578 (1989). These residues are conserved in the $D_1$ dopamine receptor (Asp 103, Ser 199, Ser 202). The postulated structural organization of this receptor predicts a short third cytoplasmic loop (54 amino acids) between transmembrane domains V and VI and a long carboxyl terminus (110 amino acids). These features resemble the organization of other receptors coupled to $G_s$, e.g., $\beta_1$- and $\beta_2$-adrenergic receptors. In addition, it is interesting to note that the sequence of the human $D_1$ receptor at the amino terminal of the third cytoplasmic loop (RIYRIAQKQIRRI; amino acids 216–228) is very similar to the same region of the human $b_1$-adrenergic receptor (RVFREAQKQVKKI; amino acids 246–258). Mutagenesis studies have suggested that this intracellular loop has an important role in coupling receptors to their respective G proteins. See O'Dowd, B. et al., J. Biol. Chem. 263, 15985–15992 (1988). Thus, this sequence in the $D_1$ receptor may selectively promote its interaction with $G_s$.

EXAMPLE 2

Binding of $D_1$ Receptor Antagonist SCH23982 to Membranes of COS-7 Cells Expressing HGL26

To identify the protein encoded by genomic clone HGL26, a 2.3 kb EcoRI-XbaI restriction fragment containing the open reading frame was subcloned into the expression vector pCMV5 and transiently transfected into African green monkey kidney (COS-7) cells. See Andersson, S. et al., J. Biol. Chem. 264, 8222–8229 (1989). The DEAE-dextran method was used for transient transfection of COS-7 cells. See Cullen, B. Meth. Enzymol. 152, 684–704 (1987). After 48 hours, transfected cells were lysed and homogenized in ice-cold lysis buffer (10 mM Tris HCl, pH 7.4, 5 mM EDTA). The homogenate was centrifuged at 43,000 g for 30 min at 4° C. The resulting pellet was resuspended in lysis buffer, re-homogenized, and re-centrifuged. This pellet was resuspended in an assay buffer containing 50 mM Tris HCl, pH 7.4, 100 mM NaCl, 5 mM EDTA.

Membranes prepared from transfected COS-7 cells in the manner described above exhibited a 10- to 30-fold increase in specific binding of the $D_1$ antagonist [$^{125}$I]SCH23982 compared to cells transfected with an antisense construct. Saturation assays indicated that the apparent equilibrium dissociation constant ($K_d$) for [$^{125}$I]SCH23982 was 0.35±0.02 nM (n=6); non-specific binding was determined with 1 uM flupenthixol. These data are in good agreement with previous results obtained with rat striatal membranes. See Sidhu, A. et al., J. Eur. J. Pharmacol. 128, 213–220 (1986).

Competition assays were conducted with the transformed COS-7 cell membranes in a volume of 200 ul containing approximately 0.3 nM [$^{125}$I]SCH23982 and varying concentrations of agonists or antagonists for 1 hr at room temperature. Incubations were terminated by the addition of 5 ml of ice-cold 50 mM Tris HCl, pH 7.4, 100 mM NaCl, rapid vacuum filtration through Whatman GF/C filters, and two subsequent 5 ml washes. Nonspecific binding typically represented 3–10% of total binding. Data are average values of duplicate determinations from representative experiments and were modelled by nonlinear least square curve fitting by computer using a one-site model. See DeLean, A. et al., R. Mol. Pharmacol. 21, 5–16 (1982).

Figure 2A:
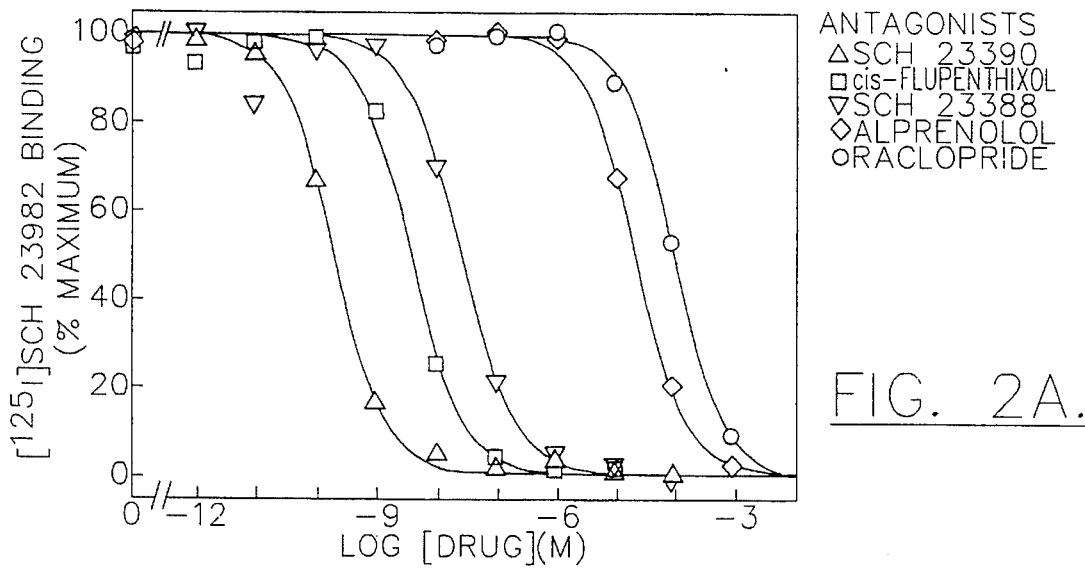
FIGS. 2A and 2B show the binding properties of the selective $D_1$ dopamine receptor antagonist [$^{125}I$]SCH23982 to membranes of COS-7 cells expressing the coding sequence of clone HGL26. Various catecholamine antagonists (FIG. 2A) or agonists (FIG. 2B) were tested for their ability to compete for the binding of [$^{125}I$]SCH23982 to membranes of COS-7 cells transfected with a pCMV5 construct of clone HGL26.
Figure 2B:
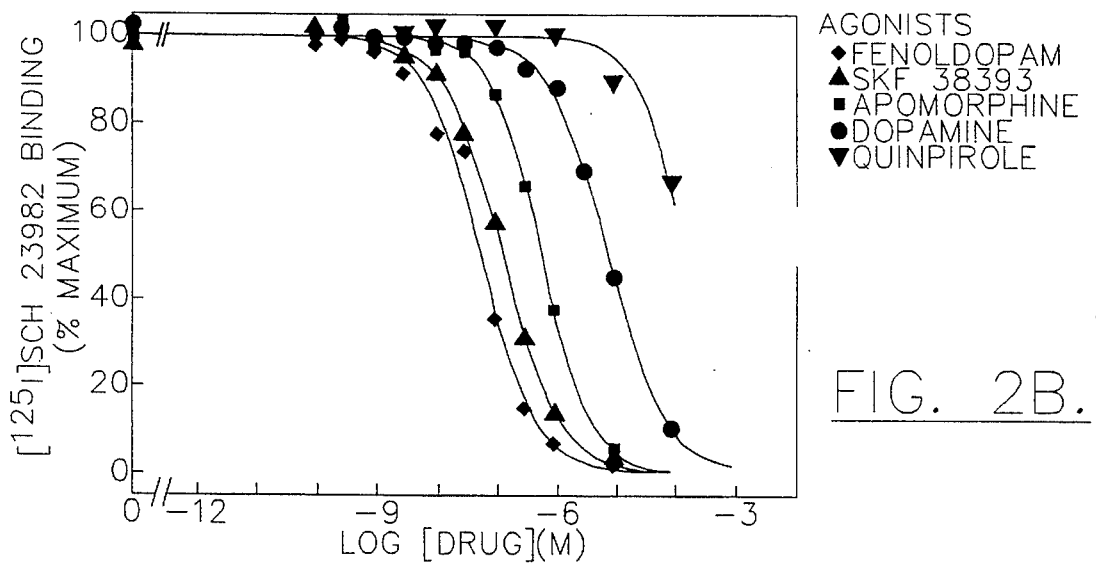

As shown in FIGS. 2A and 2B, agonists and antagonists competed for the binding of [$^{125}$I]SCH23982 with an order of potency typical of binding to a $D_1$ dopamine receptor. See Billard, W. et al., Life Sci. 35, 1885–1893 (1984); Andersen, P. et al., Life Sci. 37, 1971–1983 (1985). Thus, the gene that we have isolated codes for a protein with the pharmacological characteristics expected for a $D_1$ dopamine receptor.

EXAMPLE 3

Dopamine stimulation of Adenylyl Cyclase in Membranes Prepared From Mouse Fibroblasts Expressing Clone HGL26

Stable expression was obtained by cotransfection of a pCMV5 construct of clone HGL26 with the selection plasmid pRSVNeo into mouse fibroblast [L-M(TK$^-$)] cells using the calcium phosphate procedure. See Cullen, B. Meth. Enzymol. 152, 684–704 (1987). Transformed cells were selected for resistance to G418 (450 µg/ml) and assayed for [$^{125}$I]SCH23982 binding. For assay of adenylyl cyclase activity, cells were washed twice with ice-cold phosphate-buffered saline, scraped from the plates in ice-cold lysis buffer (5 mM Tris-HCl, 2 mM EDTA, pH 7.4), and homogenized using a Polytron cell disrupter (Brinkman). Crude membranes were pelleted by centrifugation at 43,000×g at 4° C. for 20 min, resuspended in ice-cold lysis buffer and re-centrifuged. The resulting pellet was then resuspended in 75 mM Tris-HCl, pH 7.2, 5 mM $MgCl_2$, 3 mM EDTA to ~0.2 mg protein/ml. Adenylyl cyclase activity in the membranes was measured by known procedures. See Salomon, Y., et al. Anal. Biochem. 58, 541–548 (1974). Assay mixtures contained 20 µl membranes, 30 mM Tris-HCl, pH 7.2, 2 mM $MgCl_2$, 0.8 mM EDTA, 120 µM ATP with ~1.5 µCi a[$^{32}$P]ATP/tube, 53 µM GTP, 100 µM cAMP, 2.7 mM phospho(enol)pyruvate, 0.2 IU pyruvate kinase, 1 µU myokinase, 0.02% ascorbate, and drugs of interest in a total assay volume of 50 µl. Assays, performed in triplicate, were incubated at 37° C. for 60 min and were terminated by the addition of 1 ml of 400 µM ATP, 300 µM cAMP and ~25,000 cpm of [$^3$H]cAMP. cAMP was isolated from ATP by chromatography over 1 ml Dowex and 1 ml alumina columns. Double labeled samples were counted by liquid scintillation counting.

Figure 2C:
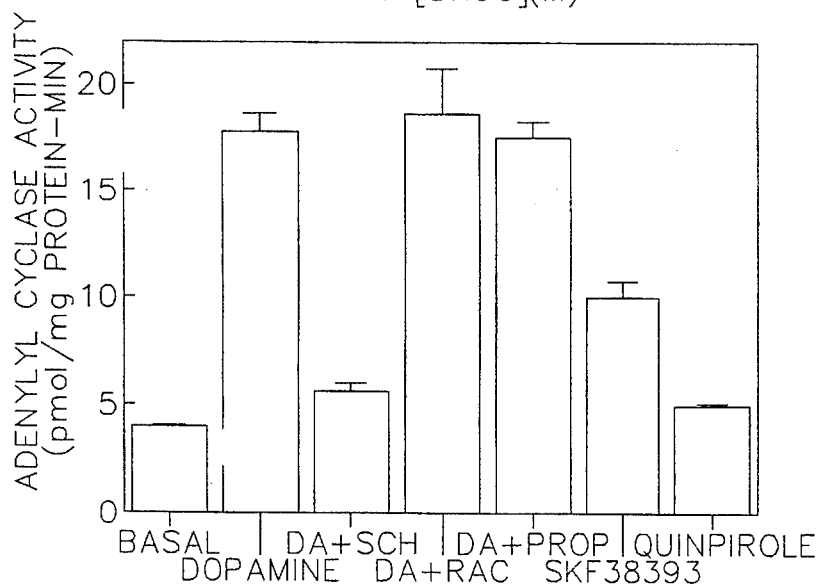
FIG. 2C shows the stimulation by dopamine of adenylyl cyclase activity in membranes prepared from mouse fibroblasts expressing the $D_1$ dopamine receptor gene coded for by HGL26. Drug concentrations: dopamine (DA), 100 μM; SCH23390 (SCH), raclopride (Rac), propranolol (Prop), SKF38393, and quinpirole, 1 μM each.

Data are shown in FIG. 2C. The $D_1$ receptor coded for by HGL26 appears to couple selectively to adenylyl cyclase. In mouse Ltk$^-$ cells transfected with the gene for the $D_1$ dopamine receptor, dopamine stimulated membrane adenylyl cyclase activity approximately 5-fold. This effect of dopamine was blocked by the $D_1$ antagonist SCH23390 but not by the $D_2$ antagonist raclopride. The $D_1$ partial agonist SKF38393 also stimulated enzyme activity, whereas the $D_2$ selective agonist quinpirole was ineffective. Similar results were obtained by measurement of dopamine-stimulated whole cell cAMP levels (data not shown). In contrast, dopamine failed to stimulate phosphatidylinositol (PI) metabolism in COS-7 cells transfected with the $D_1$ dopamine receptor construct, whereas epinephrine potently evoked this response in other COS-7 cells transfected with an $\alpha_1$-adrenergic receptor clone (data not shown). See Cotecchia, S. et al., Proc. Natl. Acad. Sci. USA 85, 7159–7163 (1988).

EXAMPLE 4

Detection of $D_1$ Dopamine Receptor mRNA in Human Tissue

Total RNA was isolated from human postmortem tissue using the guanidinium isothiocyanate/cesium chloride method. See Chirgwin, J. et al., Biochemistry 18, 5294–5299 (1979). Using 2 µg of this total RNA, an 18-mer (ATGAACATTTAGAATCTC) primer directed to the 3' untranslated region of the human $D_1$ dopamine receptor was used to synthesize first-strand cDNA using AMV-reverse transcriptase (4 U) (Bethesda Research Laboratory) under conditions previously described. Sambrook, J., Fritsch, E. and Maniatis, T. Molecular Cloning: A Laboratory Manual. (Cold Spring Harbor Laboratory Press, Cold Spring Harbor, N.Y., 1989.) In Northern blots of this human tissue, mRNA (4.2 kb) was most abundant in the caudate; somewhat lower levels were found in the cortex and cerebellum.

To detect receptor message that might be present at very low abundance, PCR was used to amplify a specific 490 bp fragment in the 3' untranslated region of the $D_1$ receptor message. See Wang, A. et al., Proc. Natl. Acad. Sci. USA 86, 9717–9721 (1989). Polymerase from *Thermus aquaticus* (1 U), the appropriate buffer, 20 µCi [$^{32}$P]dCTP, and two new 18-mer primers (CCAAATACATTCCAGTGT as 5' primer; AAATGTGGTTGTAAGGTC as 3' primer) were then added to the reaction. These components were subjected to 25 cycles of amplification (94° C., 2 min; 45° C., 2 min; 72° C., 2 min) to amplify a 490 bp segment of this first-strand cDNA template. An aliquot of each reaction was subjected to electrophoresis on a 1.5% agarose gel, transferred to a nytran membrane, washed, and exposed to X-ray film. To test for the presence of contaminating genomic DNA in the RNA from these tissues, a reaction was performed as described above but without the addition of AMV-reverse transcriptase. In this experiment, no detectable bands were amplified from 2 µg of RNA. Furthermore, primers alone without any RNA template did not give rise to any detectable product.

Using this technique, a large amount of amplified product was obtained from human caudate RNA. The next greatest amount of product was obtained from frontal cortex, followed by hippocampus, cerebellum, and ventral tegmental area. No detectable product was amplified from substantia nigra, kidney, heart, or liver. A standard curve was developed to test the linearity of the PCR amplification. The 2.3 kb EcoRI-XbaI restriction fragment of clone HGL26 was subcloned into pBluescript II SK+ (Stratagene). This construct was digested with XbaI, and RNA was synthesized using T7 RNA polymerase. The resulting product was digested with DNAse I, diluted, and 400, 40, 4, 0.4, and 0.04 femtogram (fg) of this template RNA were subjected to the procedure described above. Aliquots from each reaction were applied to a Whatman DE- 81 membrane, washed extensively in 0.5M phosphate buffer, pH 6.5, and counted by liquid scintillation spectrometry. The standard curve indicated that the amount of amplified product was proportional to the amount of template added. However, this relationship was no longer linear at higher levels of template where the amount of enzyme and primers in the reaction presumably become limiting. Thus, this method is quite sensitive for very low abundance messages but is limited by the amount of product formed when template is very abundant. Hence, in actuality, the differences observed between tissues are likely to be larger than those indicated by our data.

EXAMPLE 5

Localization of $D_1$ Receptor mRNA in Rat Brain by In Situ Hybridization

To examine more carefully the CNS distribution of the message for the $D_1$ receptor, a partial cDNA clone encoding the rat homologue of this receptor was isolated for the purpose of in situ hybridization. This Example also illustrates the use of the human clones described above to obtain a clone for a $D_1$-dopamine receptor from another species, i.e., rat.

A rat striatal cDNA library (provided by Dr. M. Ehrlich, Rockefeller Inst.) was screened ($1.5 \times 10^6$ recombinants) using the 0.7 kb PvuII restriction fragment of clone D233. Duplicate nitrocellulose filters were hybridized in 50% formamide, 5× SSC, 5× Denhardt's, 0.1 M sodium phosphate, pH 6.5, 0.1% SDS, 100 μg/ml sheared salmon sperm DNA, 10% dextran sulfate, and $2 \times 10^6$ cpm/ml [$^{32}$P]-labeled probe at 42° C. for 18 hr. Filters were washed at 55° C. in 1X SSC, 0.1% SDS. Positive plaques were identified by autoradiography. Two clones possessing identical restriction maps were isolated. EcoRI restriction fragments of 0.5 and 2.5 kb from one clone (RSL25) were subcloned and partially sequenced. A 0.45 kb EcoRI-ClaI restriction fragment from the 0.5 kb EcoRI fragment of RSL25 and a 1.5 kb SacI-BamHI restriction fragment from the rat striatal $D_2$ receptor cDNA[2] were subcloned into pBluescript (Stratagene). [$^{35}$S]-labeled antisense- or sense-strandRNA probes were prepared by in vitro transcription and hybridized with 4% paraformaldehyde-fixed sagittal rat brain sections (15 μm) as previously described. Fremeau, R. et al., Science 234, 1265–1269 (1986).

X-ray film images of rat brain sagittal section tissue hybridized with [$^{35}$S]-labeled antisense $D_1$ receptor probe revealed intense hybridization signal overlying the striatum (CPu), nucleus accumbens (AcbC), and olfactory tubercle (Tu). No specific labeling was observed over the substantia nigra (SNC), ventral tegmental area, or amygdala. X-ray film images of rat brain sagittal section tissue hybridized with [$^{35}$S]-labeled antisense $D_2$ receptor probe revealed intense hybridization signal over the CPu, AcbC, Tu, and SNC. Hybridization of serial sections with [$^{35}$S]-labeled sense-strand control probes from the $D_1$ or $D_2$ receptor clones resulted in background labeling over the CPu, AcbC, Tu, and SNC. In contrast, a similar signal to that observed with the antisense probes was detected with the sense-strand control probes over the cerebellar granular cell layer. Thus, the cerebellar signal may reflect a false positive related to the high cell density of the cerebellar granular cell layer. The lack of $D_1$ receptor mRNA in substantia nigra as determined by both PCR and in situ hybridization is consistent with previous lesion experiments suggesting that the $D_1$ receptors in this area are on terminals of the striatonigral pathway neurons. Spano, P. et al., Science 196, 1343–1345 (1977).

EXAMPLE 6

Competitive Binding Studies with COS-7 Cell Membranes Expressing Clone HGL26

Varying amounts of antagonists and agonists were used to compete for [$^{125}$I]SCH23982 binding to membranes prepared from COS-7 cells transfected with the EcoRI-XbaI restriction fragment of clone HGL26 in the expression vector pCMV5. Experiments were conducted as described in Example 2 Above. Apparent equilibrium dissociation constants ($K_d$) were determined by computer with a nonlinear regression program describing the interaction of ligands with a single class of binding sites. See DeLean, A. et al., Mol. Pharmacol. 21, 5–16 (1982). Data are given in Table 1 below. Values represent the means of 2–5 independent experimental determinations whose $pK_d$ values were within 10%.

TABLE 1

$K_d$ Values of Ligands for [$^{125}$I]SCH23982 Binding Sites

| Antagonists: | $K_d$ (nM) | Agonists: | $K_d$ (nM) |
|---|---|---|---|
| SCH23390 | 0.11 | fenoldopam | 20 |
| cis-piflutixol | 0.20 | SKF38393 | 87 |
| (+)butaclamol | 0.90 | (−)apomorphine | 210 |
| cis-flupenthixol | 1.6 | dopamine | 2,500 |
| SCH23388 | 22 | quinpirole | 14,000 |
| ketanserin | 190 | serotonin | >15,000 |
| spiperone | 220 | epinephrine | >55,000 |
| yohimbine | 1,800 | | |
| prazosin | 3,000 | | |
| (−)butaclamol | 4,900 | | |
| alprenolol | 16,000 | | |
| raclopride | >72,000 | | |

EXAMPLE 7

Chromosomal Location of the $D_1$ Receptor Gene

Chromosomal assignment of the $D_1$ dopamine receptor was determined by in situ hybridization of a [$^3$H]-labeled $D_1$ receptor probe (EcoRI-XbaI restriction fragment) to human metaphase chromosomes. See Yang-Feng, T. et al., Am. J. Human Genetics 37, 1117–1128 (1985). This probe was found to localize to the long arm of chromosome 5. It is interesting to note that the genes for several adrenergic and $5HT_{1A}$ receptors as well as those for platelet-derived growth factor and glucocorticoid receptors are all located in this region of chromosome 5. See Yang-Feng, T. et al., Proc. Natl. Acad. Sci. USA 87, 1516–1520 (1990); LeBeau, M. et al., Science 231, 984–987 (1986); Gehring, U. et al., Proc. Natl. Acad. Sci. USA 82, 3751–3756 (1985). Southern blot analysis of genomic DNA at high stringency revealed the presence of a single hybridizing band, suggesting the existence of a single copy gene. At lower stringency, however, multiple hybridizing bands were detected (data not shown).

EXAMPLE 8

Isolation of Partial Rat Striatal $D_1$ Dopamine Receptor Clone R213 by PCR

To clone the $D_1$ receptor, a set of degenerate oligonucleotide primers were designed based on the nucleotide sequences of known catecholamine receptors and some other G-protein-coupled receptors. See H. Dohlman et al., Biochemistry 26, 2657 (1987); F. Libert et al., Science 244, 569 (1989). Double-stranded cDNA was synthesized from rat striatum poly A$^+$ mRNA. Two degenerate oligonucleotides (III: GAG TCG ACC TGT G{C/T}G {C/T} {C/G}A T{C/T} {A/G} CII T{G/T}G AC{C/A} G{C/G}TA C; VI: CAG AAT TCA G{T/A}A GGG CAI CCA GCA GAI {G/C} {G/A} {T/C} GAA) were designed based on the relatively conserved regions of receptor transmembrane domains III and VI. Rat striatum cDNA served as template in 30 cycles of polymerase chain reaction (PCR), R. Saiki et al., Science 239, 487 (1988), with one minute of denaturation at 95° C., two minutes of annealing at 45° C., and three minutes of extension at 72° C. Rat striatum cDNA was chosen as the template because high levels of $D_1$ dopamine receptor have been found in this tissue. S. Boyson et al., J. Neurosci. 6, 3177 (1986). Deletion studies have shown that (he third cytoplasmic loop is crucial for G-protein coupling. B. O'Dowd et al., *J. Biol. Chem.* 263, 15985 (1988). Since the three cloned β-adrenergic receptors that couple to Gs have putative third cytoplasmic loops of 52–78 amino acids, see L. Emorine et al., *Science* 245, 1118 (1989), we hypothesized that the third cytoplasmic loop of the dopamine $D_1$ receptor might be in a similar size range. Therefore, the PCR products were double digested with EcoRI and SalI and the portion from 450 to 700 bp was extracted (GeneClean) and subcloned into M13mp18 and M13mp19 and subjected to direct sequencing. Of 24 PCR products analyzed, D2 dopamine, $\alpha_{2B}$ adrenergic and five sequences representing potentially new G-protein-coupled receptors were obtained. One of these clones, R213, had several interesting structural features. It had a higher degree of amino acid similarity with known catecholamine receptors as compared to other G-protein-coupled receptors; in the putative fifth transmembrane domain it contained two serine residues which were thought to be specific to receptors binding catecholamines; and it had a putative third cytoplasmic loop similar in size and sequence to that of the β-adrenergic receptors.

EXAMPLE 9

Screening of Rat Striatal cDNA library and Human Genomic library with Clone R213

Figure 3A:
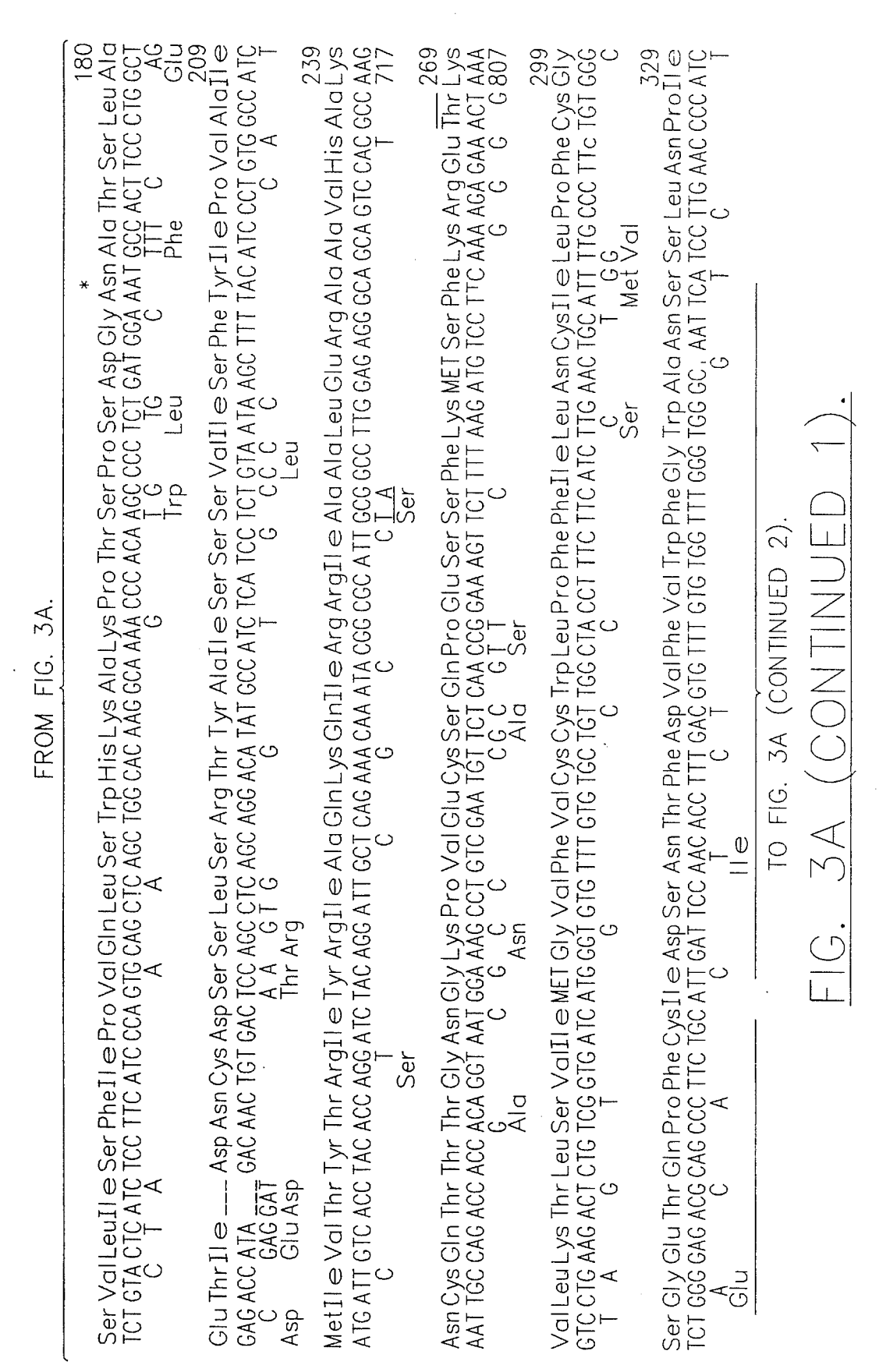
Figure 3B:
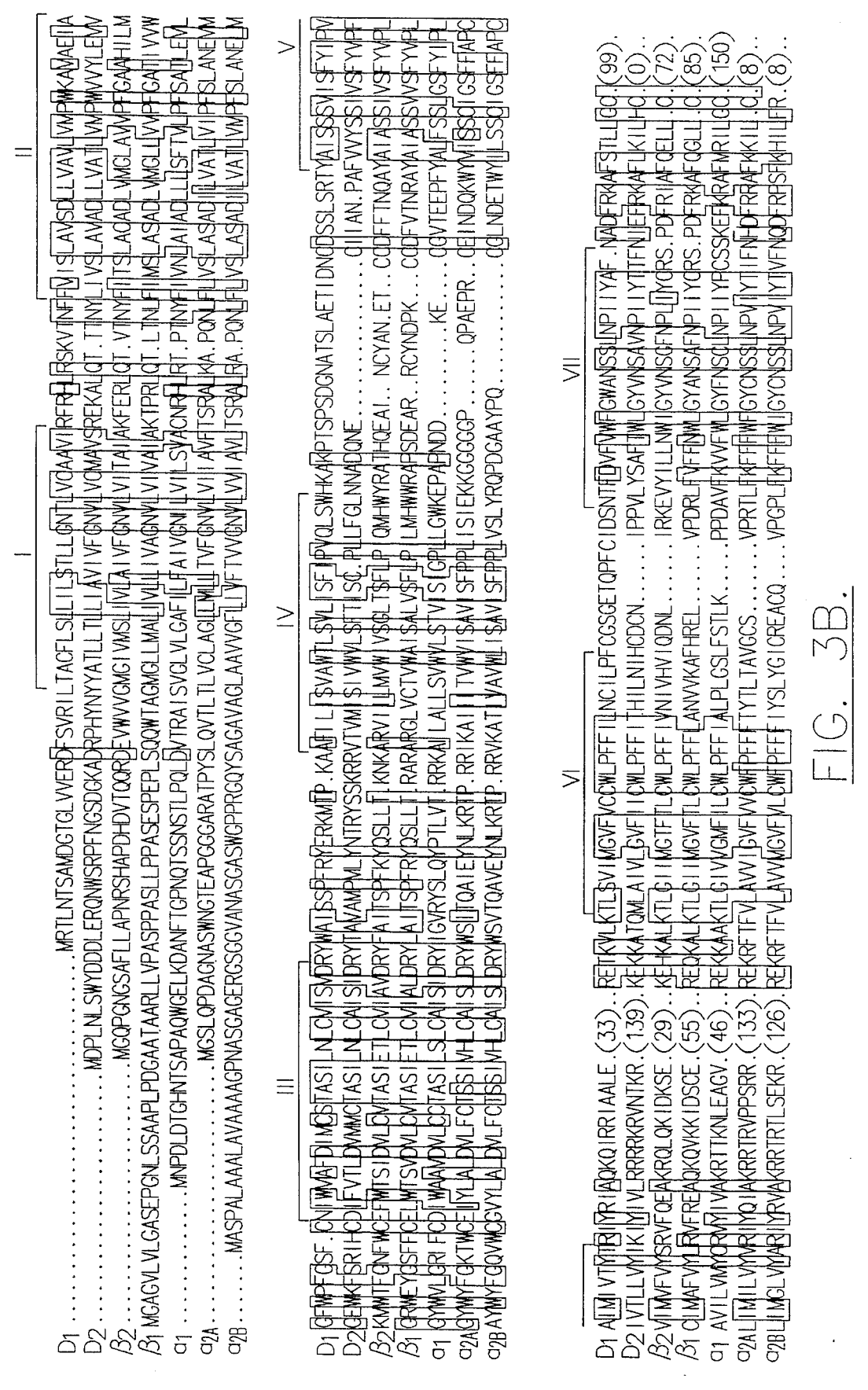

The PCR generated clone R2 13 was used as a probe to screen a rat striatum cDNA library. One positive clone was identified and sequenced. Although not full-length, it allowed us to describe most of the rat coding sequence (FIG. 3). Since most catecholamine receptors lack introns in their coding regions, see R. Lefkowitz et al., *Cold Spring Harbor Symp. Quant. Biol.* 53, 507 (1988), and since our preliminary human genomic analysis indicated the absence of introns in this gene (unpublished observations), we screened a human genomic library with R213. Eight positive signals were obtained. One clone, HGR213-1, was further characterized and a 3.0 kb EcoRI/SacI fragment spanning the whole coding region was subcloned and sequenced. The rat coding sequence was obtained by sequencing of a partial rat cDNA clone and a rat genomic clone. Sequencing was done by the Sanger dideoxy chain termination method using Sequenase (US Biochemical Corporation).

FIG. 3 shows the nucleotide sequence of clone t(GR213-1. The longest open reading frame codes for a 446 amino-acid protein (relative molecular mass Mr=49,296). This relative molecular mass is similar to the reported value of the deglycosylated form of dopamine $D_1$ receptor as determined by SDs-PAGE. Like most adrenergic receptors, but unlike the dopamine $D_2$ receptor, HGR213-1 has no intron in its coding sequence.

There are two potential in-frame initiation sites. Considering the unique potential N-linked glycosylation site in the N-terminus, the initiation site shown in FIG. 3 is most likely the one which is used. Interestingly, there exists another potential N-linked glycosylation site in the second extracellular loop.

COMPARATIVE EXAMPLE B

Comparison of the Protein Coded For by Clone HGR213-1 With Other G Protein-coupled Receptors Hydrophobicity analysis of HGR213-1 revealed seven stretches of hydrophobic amino acids that could represent transmembrane domains(data not shown). comparison of the deduced amino acid sequence of HGR213- 1 with that of other catecholamine receptors shows that the greatest similarity exists in the putative transmembrane domains where the amino acid identities are as follows: 44% with human $D_2$, 42% with human $\beta_2$, 43% with human $\beta_1$, 41% with hamster $\alpha_1$, 42% with human $\alpha_{2A}$ and 40% with human $\alpha_{2B}$. The overall degree of identity between HGR 213-1 and $D_2$ receptors is about the same as between HGR 213-1 and adrenergic receptors. Asp79 and Asp113 in the $\beta_2$-adrenergic receptor, which possibly act as counterions for the positively charged catecholamine, are present at corresponding positions in HGR213-1. Furthermore, the size and sequence of its third cytoplasmic loop and C-terminus of HGR213-1 are similar to that of β-adrenergic receptors. This suggested that this new receptor might be coupled to Gs. However, the absence of a potentially important glutamic acid residue, which is conserved in the third transmembrane domains of all three cloned β-adrenergic receptorsl, indicated that HGR213-1 probably was not a β-adrenergic-like receptor. Based on these structural features, we hypothesized that HGR213-1 could encode a dopamine $D_1$ receptor. In addition, there exist two consensus sequences (residues 133–136, 265–268) for cAMP-dependent protein kinase phosphorylation and many serines and threonines residing in the cytoplasmic loops and the relatively long C-terminus could be potential protein kinase C or receptor kinase phosphorylation sites.

EXAMPLE 10

Tissue Distribution of HGR213-1 Transcript as Determined by Northern Blot Analysis As a step towards identifying HGR213-1, the tissue distribution of its transcript was examined by Northern blot analysis. Northern blot analysis was performed as previously described except random-primed R213 was used as hybridization probe. J. Bunzow et al., *Nature* 336, 783 (1988). A messenger RNA of approximately 4 kb was found in many rat brain regions, with the highest level of expression in the basal ganglia (data not shown). HGR213-1 mRNA was undetectable in the pituitary and in the peripheral tissues we tested. This pattern of HGR213-1 messenger distribution in the central nervous system and pituitary is consistent with that of the dopamine $D_1$ receptor as determined by autoradiography and binding studies. S. Boyson et al., *J. Neurosci.* 6, 3177 (1986).

EXAMPLE 11

Binding of Dopamine Receptor Ligands to Membranes of COS-7 Cells Expressing HGR213-1

To further address its identity, HGR213-1 was transiently expressed in eukaryotic cells. The 3.0 kb EcoRI/SacI fragment of HGR213-1 was inserted between the unique HindIII and BamHI sites of eukaryotic expression vector PBC12BI and transfected into monkey kidney COS-7 cells. See B. Cullen, *Meth. Enzymol.* 152, 684 (1987). A modified calcium phosphate method was used for the transfection of COS-7 cells. See C. Chen and H. Okayama, *Molec. Cell Biol.* 7, 2745 (1987). About 45 µg plasmid DNA were used for each large 150 mm plate. At 48 h after transfection, cells were rinsed with TEM buffer(25 mM Tris pH 7.4, 6 mM MgCl2, 1 mM EDTA) and scraped off plates.

Since its structural features and mRNA tissue distribution suggested that HGR213-1 might encode a dopamine $D_1$ receptor, membranes from transfected COS-7 cells were tested for their ability to bind to the $D_1$ selective antagonist [$^3$H]SCH23390. Membranes were prepared by homogenizing cells with a ConTorque homogenizer at 4° C. in TEM buffer. The homogenate was centrifuged at 800 g for 10 min and the pellet was subjected to a second homogenization and centrifugation. Supernatants were pooled and centrifuged at 100,000 g for 1 h. The pellet was then resuspended in TEM buffer at appropriate protein concentration and stored in small aliquots at −70° C. Binding assays were performed in duplicate in a volume of 500 µl containing 50 mM Tris pH 7.4, 0.9% NaCl, 0.025% ascorbic acid, 0.001% BSA, [3H] SCH23390 (Amersham, 69 Ci mmol-1) and tested drugs. In all competition binding assays, 0.7 nM [3H]SCH23390 was inhibited by various concentrations of unlabelled drugs. Binding was initiated by the addition of membrane preparation (20–30 µg protein) and carried on at 30° C. for 1 h. Nonspecific binding was defined in the presence of 10 µM (+)Butaclamol. The samples were filtered through glass fiber filters (Schleicher and Schuell No.32) and washed three times with 4 ml ice-cold 10 mM Tris pH 7.4. The radioactivity retained on the filter was counted using a Beckman LS6800 scintillation counter. The 50% inhibitory concentration values (IC50) calculated from the curves were converted to Ki values as described. See J. Bunzow et al., *Nature* 336,783 (1988). Inhibition was fit best by assuming the existence of only one class of binding site except in the case of inhibition by the agonist SKF82526 which was best fit by assuming the presence of two classes of binding sites. A LIGAND computer program was used for data analysis and curve fitting.

Figure 4:
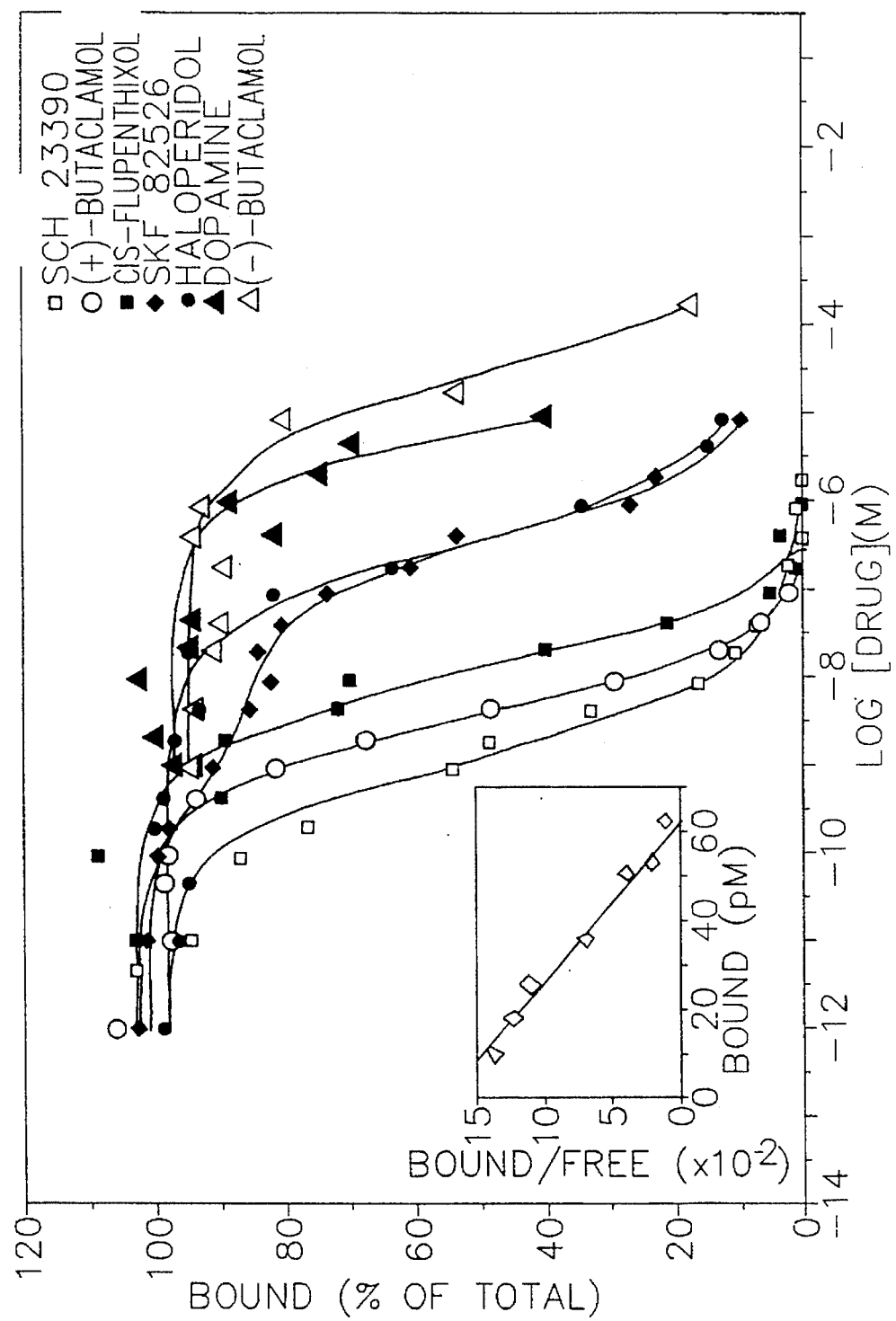
FIG. 4 shows the binding of [3H]SCH23390 to membranes prepared from COS-7 cells transfected with HGR213-1. Representative curves show the competitive inhibition of [3H]SCH23390 specific binding by different drugs. The inset shows a Scatchard transformation of saturation binding. The average Ki values from three independent experiments were: SCH23390 0.4 nM, (+)butaclamol 2.1 nM, cis-flupenthixol 5.6 nM, haloperidol 203 nM, dopamine 2.3 μM, (−)butaclamol 19 μM and SKF82526 0.2 nM (high affinity) and 150 nM (low affinity). In the Scatchard plot shown the Kd and Bmax values for membranes prepared from transfected COS-7 cells were 0.3 nM and 2 pmole per mg protein respectively.

Untransfected COS-7 cells showed no specific binding of [$^3$H]SCH23390 (data not shown). Binding of [$^3$H] SCH23390 to membranes prepared from transfected COS-7 cells was saturable with a dissociation constant (Kd) of 0.3 nM (FIG. 4 inset). This value agrees well with both the reported value29 and the value observed in parallel experiments with rat striatal membranes(data not shown). FIG. 4 shows competition curves of various ligands with [$^3$H] SCH23390. The $D_1$ selective antagonist SCH23390 and agonist SKF82526 were most potent while the $D_2$ selective antagonist haloperidol was virtually inactive. The rank order of ligand potency was: SCH23390< (+)Butaclamol>Flupenthixol>>Haloperidol. This pharmacological profile explicitly identifies the binding site as that of a dopamine $D_1$ receptor.

EXAMPLE 12

Dopamine stimulation of Adenylyl Cyclase in Membranes Prepared from Human Kidney Cells Expressing Clone HGR213-1

To demonstrate that HGR213-1 encodes a functional dopamine $D_1$ receptor we examined its ability to couple dopamine binding to activation of adenylate cyclase. Human embryonic kidney 293 cells transiently expressing HGR213-1 were tested for their ability to respond to dopamine.

Exponential growing human 293 cells (in 60-mm dishes) were transfected with 5 µg of HGR213-1 expression plasmid DNA in PBC12BI27 using a modified CAP04 method. See C. Chen and H. Okayama, *Molec. Cell Biol.* 7, 2745 (1987). The dishes were rinsed twice with DMEM plus 10% fetal calf serum after 18 h. Two days later, the plates were rinsed twice with DMEM containing 1 mg/ml BSA and 0.5 mM IBMX (3-isobutyl-1-methylxanthine). The cells were then incubated for 45 min at 37° C. in the same medium containing various drug. After aspiration of the medium, cells were washed twice with ice-cold Hanks buffered saline and lysed with 1 ml of 60% ethanol. The cell debris was collected and pelleted and the supernatants were lyophilized. The resulting pellets were resuspended in water and cAMP in each sample was quantitated using an assay method (Amersham) which measures the ability of cAMP in the sample to displace [8-3H] cAMP from a high affinity cAMP binding protein. B. Brown et al., *Biochem. J.* 171, 561 (1971). The obtained values are normalized for the number of cells on a 60-mm dish (approximately 5 times $10^5$ cells in 5A and $10^6$ cells in 5B).

Figure 5A:
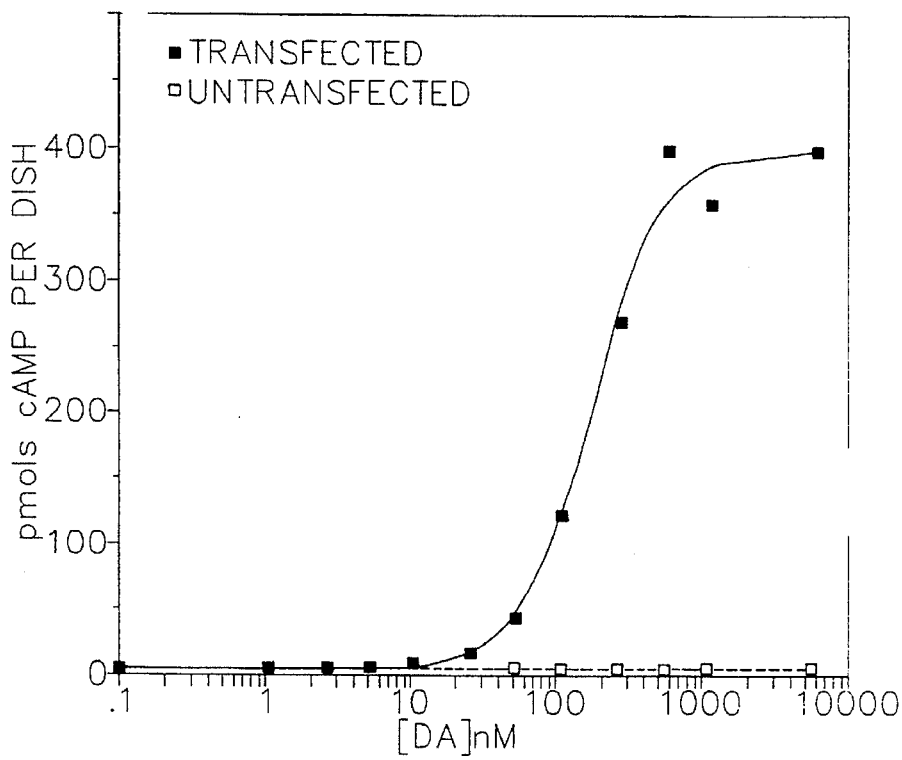
FIG. 5A shows dopamine-induced cAMP accumulation in human embryonic kidney 293 cells transfected with HGR213-1. Intracellular cAMP (ordinate) was measured as a function of dopamine (DA) concentration (abscissa) after transient expression of HGR213-1. Triplicate plates were analyzed for each point. The half-maximal stimulation concentration of dopamine (EC50) of the curve shown is 154 nM.
Figure 5B:
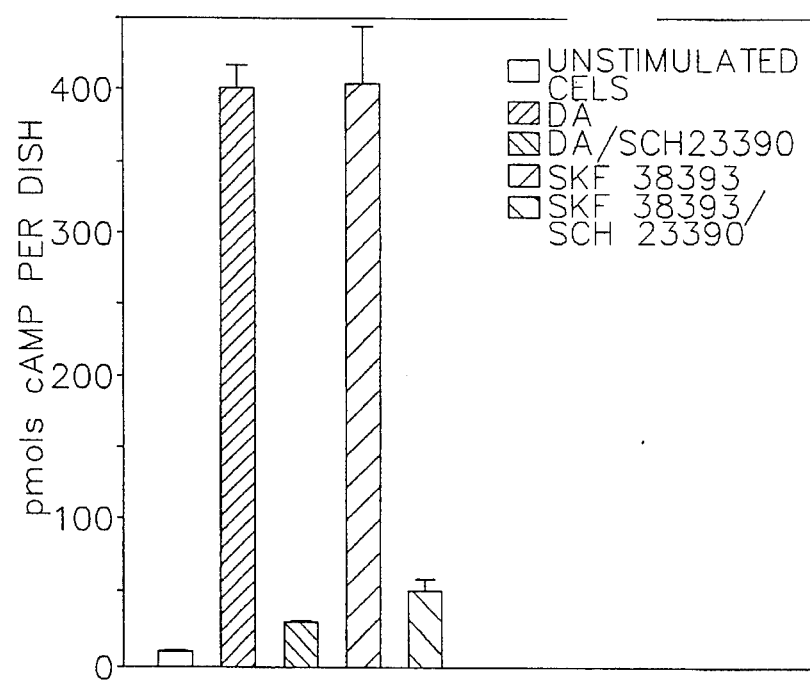
FIG. 5B shows the stimulation of cAMP accumulation in 293 cells by dopamine and SKF38393 and the antagonizing effect of SCH23390. cAMP production in 293 cells was stimulated by the agonists dopamine (125 nM) and SKF38393 (250 nM) and antagonized by SCH23390 (500 nM).

When exposed to dopamine, untransfected cells showed no elevation of cAMP (FIG. 5a). In contrast, transfected cells displayed a concentration-dependent and saturable increase of intracellular cAMP levels with a half-maximal stimulation concentration (EC50) of about 125 nM (FIG. 5a). This value is comparable to the reported value. See H. Niznik et al., *Molec. Pharmacol.* 34, 29 (1990). SKF38393, a selective D agonist, had a similar effect on the intracellular cAMP production and the stimulatory effects of both dopamine and SKF38393 were blocked by SCH23390 (FIG. 5b). These results indicated that the cloned $D_1$ receptor could couple positively to adenylate cyclase. Accordingly, we concluded that HGR213-1 encodes a human $D_1$ dopamine receptor.

The foregoing examples are illustrative of the present invention, and are not to be construed as limiting thereof. The invention is defined by the following claims, with equivalents of the claims to be included therein.

That which is claimed is:

1. An aqueous solution containing cell membranes, said cell membranes containing a $D_1$-dopamine receptor, wherein said cell membranes are free of $D_2$-dopamine receptors;
   wherein said $D_1$-dopamine receptor is encoded by a cloned isolated gene encoding a mammalian $D_1$-dopamine receptor selected from the group consisting of:
   (a) isolated DNA encoding the human $D_1$-dopamine receptor depicted in FIG. 1B(I) to 1B(III), or an isolated DNA encoding the rat $D_1$-dopamine receptor depicted in FIG. 3A; and
   (b) isolated natural mammalian DNA which hybridizes to isolated DNA of (a) above under conditions defined by a wash stringency of 1× SSC at 55° C. and encodes a $D_1$-dopamine receptor.

2. An aqueous solution according to claim 1, said cell membranes further containing adenylyl cyclase, and wherein said $D_1$-dopamine receptors is capable of stimulating said adenylyl cyclase on binding a $D_1$-dopamine receptor agonist.

3. An aqueous solution according to claim 1, wherein said $D_1$-dopamine receptor is a human $D_1$-dopamine receptor.

4. An aqueous solution according to claim 1, wherein said cell membranes are mammalian cell membranes.

5. An assay procedure comprising the steps of:
   providing an aqueous solution containing cell membranes, the cell membranes containing a $D_1$-dopamine receptor, wherein the cell membranes are free of $D_2$-dopamine receptors;
   adding a test compound to the aqueous solution; and then
   monitoring the binding of the test compound to the $D_1$-dopamine receptor;
   wherein said $D_1$-dopamine receptor is encoded by a cloned isolated gene encoding a mammalian $D_1$-dopamine receptor selected from the group consisting of:
   (a) isolated DNA encoding the human $D_1$-dopamine receptor depicted in FIG. 1B(I) to 1B(III), or an isolated DNA encoding the rat $D_1$-dopamine receptor depicted in FIG. 3A; and (b) isolated natural mammalian DNA which hybridizes to isolated DNA of (a) above under conditions defined by a wash stringency of 1X SSC at 55° C. and encodes a $D_1$-dopamine receptor.

6. An assay procedure according to claim 5, wherein:

said cell membranes further contain adenylyl cyclase, and wherein the $D_1$-dopamine receptors is capable of stimulating the adenylyl cyclase on binding a $D_1$-dopamine receptor agonist; and wherein said step of monitoring the binding of the test compound to the $D_1$-dopamine receptors comprises monitoring the activity of adenylyl cyclase in the aqueous solution.

7. An assay procedure according to claim 5, wherein said $D_1$-dopamine receptor is a human $D_1$-dopamine receptor.

8. An assay procedure according to claim 5, wherein said cell membranes are mammalian cell membranes.

* * * * *

UNITED STATES PATENT AND TRADEMARK OFFICE
CERTIFICATE OF CORRECTION

PATENT NO. : 5,547,845
DATED : August 20, 1996
INVENTOR(S) : James R. Bunzow, Olivier Civelli, David K. Grandy and Qun Y. Zhou It is certified that error appears in the above-identified patent and that said Letters Patent is hereby corrected as shown below:

Title page, item [75], add the following inventors:
--Marc G. Caron; Allen (NMN) Dearry; Pierre (NMN) Falardeau and Jay A. Gingrich; all of Durham, NC-- before James R. Bunzow.

Column 2, line 61, please correct "[$^{125}$ISCH23982" to read --[$^{125}$I]SCH23982--.

Column 15, line 1, please correct "(he" to read --the--.

Column 15, lines 44 and 45, please correct "t(GR213-1." to read --HGR213-1--.

Column 15, line 65, please correct "comparison" to read --Comparison--

Column 17, line 39, please correct "SCH23390<" to read --SCH23390>--

Signed and Sealed this

Eighteenth Day of March, 1997

Attest:

BRUCE LEHMAN

Attesting Officer    Commissioner of Patents and Trademarks